US010329232B2

(12) United States Patent
Jabin et al.

(10) Patent No.: US 10,329,232 B2
(45) Date of Patent: Jun. 25, 2019

(54) MATERIALS COATED WITH CALIXARENES

(71) Applicants: UNIVERSITE LIBRE DE BRUXELLES (ULB), Brussels (BE); CENTER NATIONAL DE LA RECHERCHE SCIENTIFIQUE—CNRS, Paris (FR); UNIVERSITE DE RENNES 1, CS (FR); UNIVERSITE PARIS DESCARTES, Paris (FR)

(72) Inventors: Ivan Jabin, Brussels (BE); Alice Mattiuzzi, Montigny-le-Tilleul (BE); Corlnne Lagrost, Hede-Bazouges (FR); Philippe Hapiot, Acigné (FR); Olivia Reinaud, Paris (FR)

(73) Assignees: UNIVERSITE LIBRE DE BRUXELLES (ULB), Brussels (BE); CENTER NATIONAL DE LA RECHERCHE SCIENTIFIQUE—CNRS, Paris (FR); UNIVERSITE DE RENNES 1, Rennes (FR); UNIVERSITE PARIS DESCARTES, Paris (FR)

( * ) Notice: Subject to any disclaimer, the term of this patent is extended or adjusted under 35 U.S.C. 154(b) by 1071 days.

(21) Appl. No.: 14/391,651

(22) PCT Filed: Mar. 28, 2013

(86) PCT No.: PCT/EP2013/056789
§ 371 (c)(1),
(2) Date: Oct. 9, 2014

(87) PCT Pub. No.: WO2013/152967
PCT Pub. Date: Oct. 17, 2013

(65) Prior Publication Data
US 2015/0064455 A1  Mar. 5, 2015

(30) Foreign Application Priority Data

Apr. 13, 2012 (EP) .................... 12164038

(51) Int. Cl.
*C08J 7/04* (2006.01)
*C07C 43/21* (2006.01)
(Continued)

(52) U.S. Cl.
CPC ............ *C07C 43/21* (2013.01); *C07C 43/225* (2013.01); *C07C 59/72* (2013.01); *C07C 69/736* (2013.01);
(Continued)

(58) Field of Classification Search
None
See application file for complete search history.

(56) References Cited

U.S. PATENT DOCUMENTS 8,133,549 B2    3/2012  Bureau
2003/0228974 A1*  12/2003  Katz .................... B01J 20/3204
                                                      502/150
(Continued)

FOREIGN PATENT DOCUMENTS

WO    2009069980    6/2009

OTHER PUBLICATIONS

Van Gelder, et al., "Preparation and Conformation of Monohalotetrahydroxycalix[5]arenes", J. Org. Chem, 1996, 61, 8419-8424.*
(Continued)

*Primary Examiner* — Scott R. Walshon
*Assistant Examiner* — Elaine M Vazquez
(74) *Attorney, Agent, or Firm* — Duane Morris LLP; Gregory M. Lefkowitz; Jason M. Nolan

(57) ABSTRACT

A calixarene directly grafted onto the surface of a material, a related grafting process, and certain calixarene intermediates useful for carrying out the grafting process.

16 Claims, 1 Drawing Sheet

(51) Int. Cl.
  C07C 59/72    (2006.01)
  C07C 205/37   (2006.01)
  C07C 217/94   (2006.01)
  C07C 245/20   (2006.01)
  C07C 43/225   (2006.01)
  C07C 69/736   (2006.01)
  C07D 333/50   (2006.01)
(52) U.S. Cl.
  CPC .......... *C07C 205/37* (2013.01); *C07C 217/94* (2013.01); *C07C 245/20* (2013.01); *C07D 333/50* (2013.01); *C08J 7/04* (2013.01); *C07B 2200/11* (2013.01); *C07C 2603/90* (2017.05); *Y10T 428/265* (2015.01)

(56) References Cited

U.S. PATENT DOCUMENTS

2008/0193668 A1    8/2008   Mevellec et al.
2013/0004885 A1*   1/2013   Strmcnik ............ C23C 22/02
                                                   429/524

OTHER PUBLICATIONS

Alice Mattiuzzi et al: "Electrografting of calix[4]arenediazonium salts to form versatile robust platforms for spatially controlled surface functionalization", Nature Communications, vol. 3, Oct. 16, 2012 (Oct. 16, 2012), pp. 1130/1-1130/8, XP009170591, ISSN: 2041-1723.

N. Toumi et al: "Grafting of calix[4]arene derivative on activated carbon surface", Materials Science and Engineering C, vol. 26, 2006, p. 490, XP002681379.

Xiaoguang Yang et al: "Synthesis and NLO properties of polar self-assemblies of molecular pyramids covalently bound on oxide surfaces", Angew. Chem. Int. Ed. Engl. 1996, 35, N° 5, vol. 35, 1996, p. 538, XP002681378.

Chen et al., "Comparative Study of Protein Immobilization Properties on Calixarene Monolayers", Sensors, vol. 7, Issue 7, MDPI (http://www.mdpi.org), Jun. 29, 2007, 12 pages.

Chen et al., "Enhancement of BSA Binding on Au Surfaces by calix[4]bisazacrown Monolayer", Sensors, vol. 7, MDPI (http://www.mdpi.org), 2007, pp. 2263-2272.

* cited by examiner

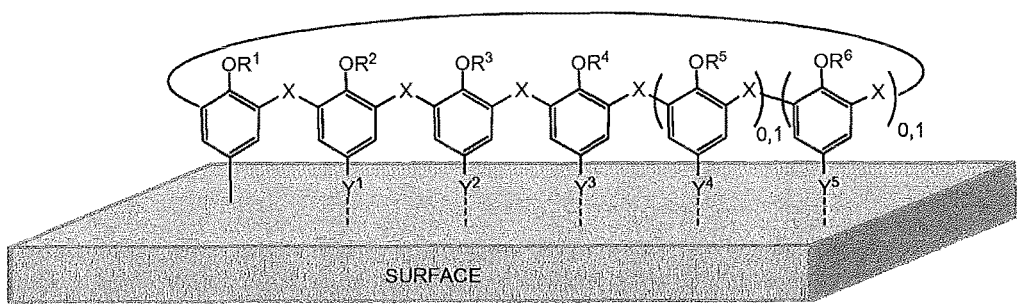

MATERIALS COATED WITH CALIXARENES

CROSS-REFERENCE TO RELATED APPLICATIONS

This application is a § 371 national stage entry of International Application No. PCT/EP2013/056789, filed Mar. 28, 2013, which claims priority to European Patent Application No. 12164038.7, filed Apr. 13, 2012, the entire contents of which are incorporated herein by reference.

FIELD OF THE INVENTION

This invention concerns materials coated with an ultra-thin layer of calix[n]arenes and thiacalix[n]arenes (n=4, 5, or 6) as well as processes for coating these materials. The invention further concerns the calix[n]arene and thiacalix[n]arene diazonium salts used in the coating process as well as the corresponding anilines.

BACKGROUND OF THE INVENTION

The electrochemical, chemical or thermal grafting on conducting, semiconducting, or non-conducting materials using aryldiazonium salts is a recognized method for surface functionalization, which has gained tremendous interest over the past decade. The organic layers obtained by this method not only are generally highly stable, much more than those formed by self-assembly chemistry, but also are strongly resistant to heat, chemical degradation and ultra-sonication. Furthermore, the method is easy to process and fast (deposition time on the order of 10 s instead of 10-18 h for thiol chemisorption onto Au substrates forming self-assembled monolayers). A major disadvantage is that highly reactive aryl radicals are involved. These attack not only the electrode surface but also already-grafted aryl layers, yielding multi-layers with ramifications, whose structure is, in general, poorly defined. The vertical extension (away from the surface) of the layers is very difficult to control, limiting the possibility of the method in designing complex patterning.

The grafting of material surfaces with aryldiazonium salts has been described in US 2009/0301862, which teaches grafting on non-conducting (insulator) or semi-conducting surfaces, on binary or ternary compounds, and on composite materials. US 2008/0193668 describes forming a film on a support material by chemically grafting aryldiazonium salts. However, grafting with aryldiazonium salts leads to the formation of disorganized multilayers. The formation of monolayers has been proposed through the adequate choice of experimental conditions (including concentration of diazonium salts, applied potential, electrolysis time when electrochemically-driven, solvent . . . ). However, this empirical control of the vertical propagation of diazonium grafting is laborious and, finally, hardly reliable. More recent work reported alternative strategies based on the design of a specific architecture of the diazonium salts. Sterically encumbered substituents on the aryl ring have been exploited to prevent polymerization reactions from taking place, allowing the formation of a near-monolayer of such molecules. A great disadvantage is that the sterically encumbered substituents render these molecules chemically inert thereby precluding any further functionalization.

Other elegant approaches use a formation-degradation sequence. It consists in preparing aryldiazonium salts with a pendant protecting group exhibiting structural or electronic shielding properties. Removal of the protecting group and subsequent post-functionalization allows for attaching functional molecules on the remaining monolayer. These strategies are efficient but require a two-step procedure for the formation of the functionalizable monolayers. Furthermore, void spaces between two adjacent molecules after the deprotection step may be created, being disadvantageous when compact, pinholes-free, layers are required. Very recent work describes a one-step strategy based on the reductive electrografting of a benzene(p-bisdiazonium) salt, leaving a diazonium pendant group for further chemical coupling. However, this approach suffers from a lack of long-term stability of the terminated diazonium layers.

One class of organic substances that has been proposed for immobilizing or grafting onto material surfaces is that of the calix[n]arenes. Calix[n]arenes are cyclic phenoxy derivatives in which n is the number of phenoxy groups, linked in their ortho positions by methylene bridges. Calixarenes are conformationally flexible molecules possessing the ability to undergo complete ring inversions that can display different conformations. Calixarenes can eventually possess a cup-like structure having a narrow and a large rim. Thiacalix[n]arenes are similar to calix[n]arenes except for the bridges that are sulfur ones.

In the following, the term "(thia)calix[n]arenes" refers to both families of compounds, those with methylene bridges (named calix[n]arenes), and those with S bridges (named thiacalix[n]arenes) and their oxide derivatives (SO and $SO_2$ bridges). In addition, (thia)calix[n]arenes also have varying numbers of phenoxy moieties expressed by the symbol [n], wherein n represents the number of phenoxy moieties, in particular n can be 4, 5, or 6. (Thia)calix[n]arenes are known compounds that have been synthesized with various substitution patterns, for example with substituents on the aromatic part of the phenoxy moieties or on its hydroxyls. These cyclic compounds find application in a manifold of areas, including the use as enzyme mimetics, ion sensitive electrodes or sensors, selective membranes, non-linear optics, and in HPLC stationary phases.

(Thia)calix[n]arenes have been used as coatings on various materials. The immobilization of (thia)calixarenes onto a surface has been reported using self-assembly techniques. The resulting immobilized calixarenes were applied as receptors.

US 2003/0228974 describes calixarene derivatives that are immobilized on a metallic or non-metallic oxide surface that has been modified by treatment with a metallic or non-metallic halides, for example silica treated with $SiCl_4$. This approach does not lead to a dense coverage of the metallic or non-metallic oxide surface, and results in branched-off structures, either via the metallic or non-metallic polyhalide link or via the phenolic hydroxyl moieties.

In most of the cases, grafting was achieved by anchoring the small rim of calixarenes onto the substrate. Only rare examples describe grafting via the large rim and, in all cases, it was achieved through thiol chemisorption (*Sensors* 2007, 7, 1091-1107; *Sensors* 2007, 7, 2263-2272 and WO 2009/069980).

Yang et al in *Angewandte Chem. Intl. Ed.* (1996) 35(5) 538-541 describe a calixarene having 4-pyridyl-aldimino arms which covalently bond, through the nitrogen atom of the pyridyl group, to the p-methyl group of a silane coupling agent of a silicone wafer or a fused silica substrate.

There is a need for materials grafted on their surface with a highly robust, structurally regular, ultra-thin layer, which layer preferably is a monomolecular layer. There is a further need for materials grafted with a layer that may serve as a platform for anchoring further molecular entities, which layer may allow spatial pre-organization and pre-structuration as well as the orthogonal polyfunctionalization of the platforms, with a precise spatial control. In addition, there is a need for providing materials grafted with a rather dense (little free surface of the coated material being present) layer. Indeed, for certain applications, it is important to control the surface density, e.g. for applications as sensors, because this may have an impact on the detection sensitivity and efficiency.

SUMMARY OF THE INVENTION

In accordance with the present invention, materials are grafted or coated with an ultra-thin layer by anchoring (thia)calix[n]arenes via their large rim at the material surface. This leads to the formation of a robust ultra-thin layer, which may be rather dense and, which, if desired, can serve as a platform for one or more further functionalization(s).

To this purpose (thia)calix[n]arenes are functionalized on the large rim by one to n amino groups, which amino functionalized (thia)calix[n]arenes can be converted in a convenient process to (thia)calix[n]aryldiazonium salts, which subsequently are grafted or coated on the surface of a material in a simple and straightforward process by means of electrochemical, chemical or thermal grafting reaction. During the grafting reaction, $N_2$ is removed from the diazonium salt so that, in contrast to the process of Yang et al cited above, the (thia)calix[n]arene moiety is directly anchored to the surface of the material through a carbon atom of the arene ring, not via a linker. Further the coated (thia)calix[n] arene layer usually has a very low thickness of about 1 to 4 nm. To our knowledge this type of direct anchoring of an ultra-thin layer has not been achieved previously.

The type of material to which the concept of the present invention is applicable is not particularly limited but includes both inorganic materials such as metals, metal alloys and metal compounds (e.g. metal oxides), nanoparticles, organic materials such as carbon, carbon nanotubes, and silicon-based materials such as, but not limited to, silica, silicon wafers, glass beads and the like, details of which are described hereinafter.

By this approach, the (thia)calixarenes are grafted via the large rim, and it leads to rigid and stable molecular layers. The latter offer a robust and stable platform for further functionalization. The macrocyclic structure of the calixarene prevents polymerization during the grafting process, induces spatial pre-organization and pre-structuration and allows the orthogonal polyfunctionalization of the platforms, with a precise spatial control.

Hence, one aspect of the present invention concerns a material grafted on its surface with an ultra-thin layer of substituted (thia)calix[n]aryl groups. Such grafted materials can be as represented as in FIG. 1. Each of the aromatic subunits of the calixarene can adopt either an "up" or a "down" orientation towards the grafted surface. "Up" orientation refers to the phenolic groups pointing in the direction of the surface and "down" orientation refers to the phenolic groups pointing in the opposite direction, away from the surface. In one embodiment, the ultra-thin layer of substituted (thia)calix[n]aryl groups is a monolayer. In FIG. 1:

X represents $CH_2$, S, SO or $SO_2$;

$R^1$, $R^2$, $R^3$, $R^4$, $R^5$ and $R^6$ each independently represent hydrogen or $C_{1-30}$ alkyl optionally substituted with one or more substituents each independently selected from the group consisting of halo (e.g. fluoro, chloro, bromo, iodo), carboxylic acid ester, alkyl or benzyl thioester, alkenyl, alkynyl, $C_{1-30}$ alkoxy, aryl, substituted aryl (wherein the substituent is fluoro or cyano or $C_{1-30}$ alkyl or $C_{1-30}$ alkoxy), —$N_3$, cyano, carboxylic acid, carboxylic acid amide, —OH, amino, amido, imino, carbamate, acyl chloride, ureido, thioureido, mercapto, substituted disulfide, heterocyclic, amino acid and amino acid derivative, peptide, phosphine or phosphine oxide, crown ether, aza-crown ether, cryptand, porphyrin, calixarene, cyclodextrin, resorcinarene, saccharide, and polyethylene glycol; and wherein two or more of $R^1$, $R^2$, $R^3$, $R^4$, $R^5$ and $R^6$ may be covalently linked either directly or by a bridge that includes oxygen, phosphine, phosphine oxide, sulfur, SO, $SO_2$, amino, imino, amido, ureido, thioureido, ester, thioester, alkene, alkyne or alkyl;

$Y^1$—, $Y^2$—, $Y^3$—, $Y^4$— and $Y^5$— each independently represent a covalent link with the material's surface, or $Y^1$—, $Y^2$—, $Y^3$—, $Y^4$— and $Y^5$— each independently selected from the group consisting of OH, hydrogen, $NO_2$, halogen, $C_{1-30}$ angle, acyle, acid carboxylic and derivatives (e.g. ester, amide), —$N_3$ alkenyl or alkynyl.

The index "0.1" at the right side of the aryl moieties bearing $R^5$ and $R^6$ means that these aryl moieties, each independently, can be present or absent.

A further aspect of this invention concerns a process of grafting a conducting or semi-conducting or non conducting material with an ultra-thin layer of substituted (thia)calix[n] aryl groups via their large rim, wherein the process comprises the deposition or grafting on the surface of a conducting or semiconducting or non conducting material of (thia)calix[n]aryl groups by the reduction of substituted (thia)calix[n]aryl salts of formula I.

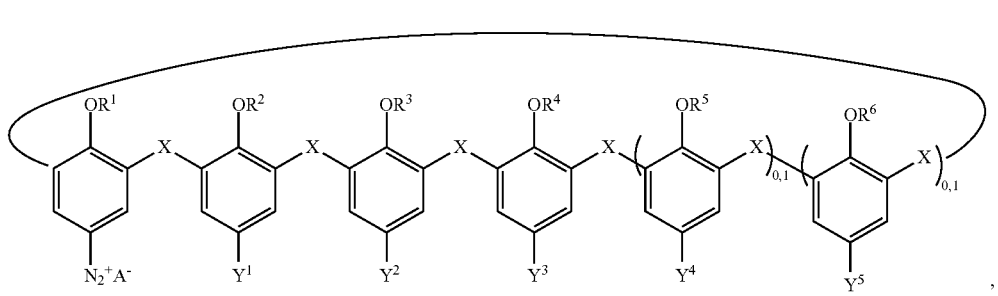

(I)

wherein X is as defined above; $R^1$, $R^2$, $R^3$, $R^4$, $R^5$ and $R^6$ are as defined above; $A^-$ represents an anion; $Y^1$, $Y^2$, $Y^3$, $Y^4$ and $Y^5$ each independently represent OH, H, $NO_2$, halogen $C_{1-30}$ alkyl, acyle, carboxylic acid and derivatives thereof (e.g. ester, amide), —$N_3$ alkenyl, alkynyl. or —$N_2^+A^-$.

In one embodiment of the present invention, the ultra-thin layer of substituted (thia)calix[n]aryl groups is a monolayer.

In still a further aspect, the present invention relates to (thia)calix[n]arene-diazonium salts of formula I, wherein X, $R^1$, $R^2$, $R^3$, $R^4$, $R^5$, $R^6$, $Y^1$, $Y^2$, $Y^3$, $Y^4$, $Y^5$, and $A^-$ are as specified herein.

The (thia)calix[n]arenes functionalized on the large rim by one or more amino groups (i.e. (thia)calix[n]-anilines) can be converted into the corresponding (thia)calix[n]-diazonium salts either by in situ diazotation of the amino groups or by diazotation followed by isolation of the diazonium salts of formula I.

In another aspect, this invention relates to (thia)calix[n]-anilines of formula:

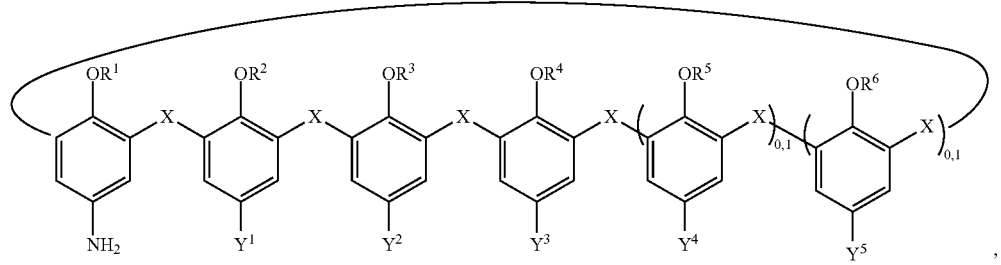

(II)

wherein X, $R^1$, $R^2$, $R^3$, $R^4$, $R^5$ and $R^6$ are as defined herein; $Y^1$, $Y^2$, $Y^3$, and, if present, $Y^4$ and $Y^5$ each independently represent $NH_2$, OH, H, $NO_2$, halogen; provided that the compound of formula (II) is not a calix[4]arene wherein X=$CH_2$, $R^1$=$R^2$=$R^3$=$R^4$=Pr, $Y^1$=$Y^2$=$Y^3$=$NH_2$ or a calix[4]arene wherein X=$CH_2$, $R_1$=$R_2$=$R_3$=Pr and $R^4$=$CH_2$COOEt, $Y^1$=$Y^2$=$Y^3$=$NH_2$, and preferably provided that the compound of formula (II) is not a calix[4]arene wherein X=$CH_2$, $R^1$=$R^2$=$R^3$=$R^4$=OH, $Y^1$=$Y^2$=$Y^3$=$NH_2$, or a calix[4]arene wherein X=$CH_2$, $R^1$=$R^2$=$R^3$=$R^4$=decyl, $Y^1$=$NH_2$, $Y^2$=$Y^3$=H, or a calix[4]arene wherein X=$CH_2$, $R^1$=$R^2$=$R^3$=$R^4$=decyl, $Y^2$=$NH_2$ $Y^1$=$Y^3$=H, or a calix[4]arene wherein X=$CH_2$, $R^1$=$R^2$=$R^3$=$R^4$=decyl, $Y^1$=$Y^2$=$Y^3$=H, or a calix[4]arene wherein X=$CH_2$, $R^1$=$R^2$=$R^3$=$R^4$=Pr, $Y^1$=$NH_2$, $Y^2$=$Y^3$=H, or a calix[4]arene wherein X=$CH_2$, $R^1$=$R^2$=$R^3$=$R^4$=Pr, $Y^2$=$NH_2$ $Y^1$=$Y^3$=H, or a calix[4]arene wherein X=$CH_2$, $R^1$=$R^2$=$R^3$=$R^4$=Pr, $Y^1$=$Y^2$=$Y^3$=H, or a calix[4]arene wherein X=$CH_2$, $R^1$=$R^3$=OH, $R^2$=$R^4$=Me, $Y^2$=$NH_2$, $Y^1$=$Y^3$=H, or a calix[4]arene wherein X=$CH_2$, $R^1$=$R^2$=$R^3$=$R^4$=Me, $Y^1$=$Y^2$=$Y^3$=$NH_2$, or a calix[4]arene wherein X=$CH_2$, $R^1$=$R^2$=$R^3$=$R^4$=Me, $Y^2$=$NH_2$, $Y^1$=$Y^3$=H, or a calix[4]arene wherein X=$CH_2$, $R^1$=$R^3$=OH, $R^2$=$R^4$=Pr, $Y^2$=$NH_2$, $Y^1$=$Y^3$=H, a calix[4]arene wherein X=$CH_2$, $R^1$=$R^2$=$R^3$=$R^4$=undecyl, $Y^1$=$Y^2$=$Y^3$=$NH_2$, a calix[4]arene wherein X=$CH_2$, $R^1$=$R^2$=$R^3$=$R^4$=pentyl, $Y^1$=$Y^2$=$Y^3$=$NH_2$, or a calix[4]arene wherein X=$CH_2$, $R^1$=$R^2$=$R^3$=$R^4$=$CH_2$COOEt, $Y^2$=$NH_2$, $Y^1$=$Y^3$=H, or a calix[4]arene wherein X=$CH_2$, $R^1$=$R^3$=$CH_2$COOEt, $R^2$=$R^4$=Me, $Y^2$=$NH_2$, $Y^1$=$Y^3$=H, or a calix[4]arene wherein X=$CH_2$, $R^1$=$R^2$=$R^3$=$R^4$=hexyl, $Y^1$=$Y^2$=$Y^3$=$NH_2$, or a calix[4]arene wherein X=$CH_2$, $R^1$=$R^2$=$R^3$=$R^4$=butyl, $Y^1$=$Y^2$=$Y^3$=H, or a calix[4]arene wherein X=$CH_2$, $R^1$=$R^2$=$R^3$=$R^4$=butyl, $Y^1$=$NH_2$, $Y^2$=$Y^3$=H, or a calix[4]arene wherein X=$CH_2$, $R^1$=$R^2$=$R^3$=$R^4$=butyl, $Y^2$=$NH_2$ $Y^1$=$Y^3$=H, or a calix[4]arene wherein X=$CH_2$, $R^1$=$R^2$=$R^3$=$R^4$=butyl, $Y^1$=$Y^2$=$NH_2$ $Y^3$=H, or a calix[4]arene wherein X=$CH_2$, $R^1$=$R^2$=$R^3$=$R^4$=butyl, $Y^1$=$Y^2$=$Y^3$=$NH_2$, or a calix[4]arene wherein X=$CH_2$, $R^1$=$R^2$=$R^3$=$R^4$=octyl, $Y^1$=$Y^2$=$Y^3$=$NH_2$, or a calix[4]arene wherein X=$CH_2$, $R^1$=$R^2$=$R^3$=$R^4$=$(CH_2)_2$O$(CH_2)_2$, $Y^1$=$Y^2$=$Y^3$=H, or a calix[4]arene wherein X=$CH_2$, $R^1$=$R^2$=$R^3$=$R^4$=$(CH_2)_2$O$(CH_2)_2$, $Y^1$=$NH_2$, $Y^2$=$Y^3$=H, or a calix[4]arene wherein X=$CH_2$, $R^1$=$R^2$=$R^3$=$R^4$=$(CH_2)_2$O$(CH_2)_2$, $Y^2$=$NH_2$ $Y^1$=$Y^3$=H, or a calix[4]arene wherein X=$CH_2$, $R^1$=$R^2$=$R^3$=$R^4$=$(CH_2)_2$O$(CH_2)_2$, $Y^1$=$Y^2$=$NH_2$ $Y^3$=H, or a calix[4]arene wherein X=$CH_2$, $R^1$=$R^2$=$R^3$=$R^4$=$(CH_2)_2$O$(CH_2)_2$, $Y^1$=$Y^2$=$Y^3$=$NH_2$, or a calix[4]arene wherein X=$CH_2$, $R^1$=$R^3$=decyl, $R^2$=$R^4$=Me, $Y^1$=$Y^2$=$Y^3$=$NH_2$, or a calix[4]arene wherein X=$CH_2$, $R^1$=$R^3$=Pr, $R^2$=$R^4$=Me, $Y^1$=$Y^2$=$Y^3$=$NH_2$, or a calix[4]arene wherein X=$CH_2$, $R^1$=$R^2$=$R^3$=Me, $R^4$=Pr, $Y^1$=$Y^2$=$Y^3$=$NH_2$, or a calix[4]arene wherein X=$CH_2$, $R^1$=$R^2$=$R^3$=Pr, $R^4$=Me, $Y^1$=$Y^2$=$Y^3$=$NH_2$, or a calix[4]arene wherein X=S, $R^1$=$R^2$=$R^3$=$R^4$=OH, $Y^1$=$Y^2$=$Y^3$=$NH_2$, or a calix[5]arene wherein X=$CH_2$, $R^1$=$R^2$=$R^3$=$R^4$=$R^5$=decyl, $Y^1$=$Y^2$=$Y^3$=$Y^4$=$NH_2$, or a calix[6]arene wherein X=$CH_2$, $R^1$=$R^2$=$R^3$=$R^4$=$R^5$=$R^6$=OH, $Y^1$=$Y^2$=$Y^3$=$Y^4$=$Y^5$=$NH_2$, or a calix[6]arene wherein X=$CH_2$, $R^1$=$R^2$=$R^3$=$R^4$=$R^5$=$R^6$=Me, $Y^1$=$Y^2$=$Y^3$=$Y^4$=$Y^5$=$NH_2$, or a calix[6]arene wherein X=$CH_2$, $R^1$=$R^2$=$R^3$=$R^4$=$R^5$=$R^6$=octyl, $Y^1$=$Y^2$=$Y^3$=$Y^4$=$Y^5$=$NH_2$, or a calix[6]arene wherein X=$CH_2$, $R^1$=$R^2$=$R^3$=$R^4$=$R^5$=$R^6$=Pr, $Y^1$=$Y^2$=$Y^3$=$Y^4$=$Y^5$=$NH_2$; wherein Pr is n-propyl and Et is ethyl.

In one embodiment, in the compounds of formula II, all of $Y^1$, $Y^2$, $Y^3$, and, if present, $Y^4$ and $Y^5$ are amino; provided that the compound of formula (II) is not a calix[4]arene wherein X=$CH_2$, $R^1$=$R^2$=$R^3$=$R^4$=Pr, $Y^1$=$Y^2$=$Y^3$=$NH_2$ or a calix[4]arene wherein X=$CH_2$, $R_1$=$R_2$=$R_3$=Pr and $R^4$=$CH_2$COOEt, $Y^1$=$Y^2$=$Y^3$=$NH_2$, or a calix[4]arene wherein X=$CH_2$, $R^1$=$R^2$=$R^3$=$R^4$=OH, $Y^1$=$Y^2$=$Y^3$=$NH_2$, or a calix[4]arene wherein X=$CH_2$, $R^1$=$R^2$=$R^3$=$R^4$=decyl, $Y^1$=$NH_2$, $Y^2$=$Y^3$=H, or a calix[4]arene wherein X=$CH_2$, $R^1$=$R^2$=$R^3$=$R^4$=decyl, $Y^2$=$NH_2$ $Y^1$=$Y^3$=H, or a calix[4]arene wherein X=$CH_2$, $R^1$=$R^2$=$R^3$=$R^4$=decyl, $Y^1$=$Y^2$=$Y^3$=H, or a calix[4]arene wherein X=$CH_2$, $R^1$=$R^2$=$R^3$=$R^4$=Pr, $Y^1$=$NH_2$, $Y^2$=$Y^3$=H, or a calix[4]arene wherein X=$CH_2$, $R^1$=$R^2$=$R^3$=$R^4$=Pr, $Y^2$=$NH_2$ $Y^1$=$Y^3$=H, or a calix[4]arene wherein X=$CH_2$, $R^1$=$R^2$=$R^3$=$R^4$=Pr, $Y^1$=$Y^2$=$Y^3$=H, or a calix[4]arene wherein X=$CH_2$, $R^1$=$R^3$=OH, $R^2$=$R^4$=Me, $Y^2$=$NH_2$, $Y^1$=$Y^3$=H, or a calix[4]arene wherein X=$CH_2$, $R^1$=$R^2$=$R^3$=$R^4$=Me, $Y^1$=$Y^2$=$Y^3$=$NH_2$, or a calix[4]arene wherein X=$CH_2$, $R^1$=$R^2$=$R^3$=$R^4$=Me, $Y^2$=$NH_2$, $Y^1$=$Y^3$=H, or a calix[4]arene wherein X=$CH_2$, $R^1$=$R^3$=OH, $R^2$=$R^4$=Pr, $Y^2$=$NH_2$, $Y^1$=$Y^3$=H, a calix[4]arene wherein X=$CH_2$, $R^1$=$R^2$=$R^3$=$R^4$=undecyl, $Y^1$=$Y^2$=$Y^3$=$NH_2$, a calix[4]arene wherein X=$CH_2$, $R^1$=$R^2$=$R^3$=$R^4$=pentyl, $Y^1$=$Y^2$=$Y^3$=$NH_2$, or a calix[4]arene wherein X=$CH_2$, $R^1$=$R^2$=$R^3$=$R^4$=$CH_2$COOEt, $Y^2$=$NH_2$, $Y^1$=$Y^3$=H, or a calix

[4]arene wherein X=CH$_2$, R$^1$=R$^3$=CH$_2$COOEt, R$^2$=R$^4$=Me, Y$^2$=NH$_2$, Y$^1$=Y$^3$=H, or a calix[4]arene wherein X=CH$_2$, R$^1$=R$^2$=R$^3$=R$^4$=hexyl, Y$^1$=Y$^2$=Y$^3$=NH$_2$, or a calix[4]arene wherein X=CH$_2$, R$^1$=R$^2$=R$^3$=R$^4$=butyl, Y$^1$=Y$^2$=Y$^3$=H, or a calix[4]arene wherein X=CH$_2$, R$^1$=R$^2$=R$^3$=R$^4$=butyl, Y$^1$=NH$_2$, Y$^2$=Y$^3$=H, or a calix[4]arene wherein X=CH$_2$, R$^1$=R$^2$=R$^3$=R$^4$=butyl, Y$^2$=NH$_2$ Y$^1$=Y$^3$=H, or a calix[4]arene wherein X=CH$_2$, R$^1$=R$^2$=R$^3$=R$^4$=butyl, Y$^1$=Y$^2$=NH$_2$ Y$^3$=H, or a calix[4]arene wherein X=CH$_2$, R$^1$=R$^2$=R$^3$=R$^4$=butyl, Y$^1$=Y$^2$=Y$^3$=NH$_2$, or a calix[4]arene wherein X=CH$_2$, R$^1$=R$^2$=R$^3$=R$^4$=octyl, Y$^1$=Y$^2$=Y$^3$=NH$_2$, or a calix[4]arene wherein X=CH$_2$, R$^1$=R$^2$=R$^3$=R$^4$=(CH$_2$)$_2$O (CH$_2$)$_2$, Y$^1$=Y$^2$=Y$^3$=H, or a calix[4]arene wherein X=CH$_2$, R$^1$=R$^2$=R$^3$=R$^4$=(CH$_2$)$_2$O(CH$_2$)$_2$, Y$^1$=NH$_2$, Y$^2$=Y$^3$=H, or a calix[4]arene wherein X=CH$_2$, R$^1$=R$^2$=R$^3$=R$^4$=(CH$_2$)$_2$O (CH$_2$)$_2$, Y$^2$=NH$_2$ Y$^1$=Y$^3$=H, or a calix[4]arene wherein X=CH$_2$, R$^1$=R$^2$=R$^3$=R$^4$=(CH$_2$)$_2$O(CH$_2$)$_2$, Y$^1$=Y$^2$=NH$_2$ Y$^3$=H, or a calix[4]arene wherein X=CH$_2$, R$^1$=R$^2$=R$^3$=R$^4$= (CH$_2$)$_2$O(CH$_2$)$_2$, Y$^1$=Y$^2$=Y$^3$=NH$_2$, or a calix[4]arene wherein X=CH$_2$, R$^1$=R$^3$=decyl, R$^2$=R$^4$=Me, Y$^1$=Y$^2$=Y$^3$=NH$_2$, or a calix[4]arene wherein X=CH$_2$, R$^1$=R$^3$=Pr, R$^2$=R$^4$=Me, Y$^1$=Y$^2$=Y$^3$=NH$_2$, or a calix[4]arene wherein X=CH$_2$, R$^1$=R$^2$=R$^3$=Me, R$^4$=Pr, Y$^1$=Y$^2$=Y$^3$=NH$_2$, or a calix[4]arene wherein X=CH$_2$, R$^1$=R$^2$=R$^3$=Pr, R$^4$=Me, Y$^1$=Y$^2$=Y$^3$=NH$_2$, or a calix[4]arene wherein X=S, R$^1$=R$^2$=R$^3$=R$^4$=OH, Y$^1$=Y$^2$=Y$^3$=NH$_2$, or a calix[5]arene wherein X=CH$_2$, R$^1$=R$^2$=R$^3$=R$^4$=R$^5$=decyl, Y$^1$=Y$^2$=Y$^3$=Y$^4$=NH$_2$, or a calix[6]arene wherein X=CH$_2$, R$^1$=R$^2$=R$^3$=R$^4$=R$^5$=R$^6$=OH, Y$^1$=Y$^2$=Y$^3$=Y$^4$=Y$^5$=NH$_2$, or a calix[6]arene wherein X=CH$_2$, R$^1$=R$^2$=R$^3$=R$^4$=R$^5$=R$^6$=Me, Y$^1$=Y$^2$=Y$^3$=Y$^4$=Y$^5$=NH$_2$, or a calix[6]arene wherein X=CH$_2$, R$^1$=R$^2$=R$^3$=R$^4$=R$^5$=R$^6$=octyl, Y$^1$=Y$^2$=Y$^3$=Y$^4$=Y$^5$=NH$_2$, or a calix[6]arene wherein X=CH$_2$, R$^2$=R$^3$=R$^4$=R$^5$=R$^6$=Pr, Y$^1$=Y$^2$=Y$^3$=Y$^5$=NH$_2$.

When (thia)calix[n]arenes such as those of formulae I or II are additionally functionalized at the small rim (e.g. with appending COOH groups) are used as starting materials, grafting leads to (thia)calix[n]arenes layers on which an easy post-functionalization of the surface can be achieved.

DESCRIPTION OF THE FIGURE

FIG. 1 schematically shows a material directly grafted on its surface with substituted (thia)calix[n]aryl groups.

DETAILED DESCRIPTION OF THE INVENTION

The term "about" when used in relation to a numerical value has the meaning generally known in the relevant art. In certain embodiments the term "about" may be left out or it may be interpreted to mean the numerical value ±10%; or ±5%; or ±2%; or ±1%.

Any feature described in relation to an aspect or embodiment can be applied to one or more of the other aspects or embodiments described herein. Features of other aspects or embodiments can be combined with the features described in relation to a particular aspect or embodiment.

Any reference cited herein is hereby incorporated by reference.

As used herein the term "material" refers to a conducting, semi-conducting, or non-conducting (insulator) material; or to composite materials, or to composite materials comprising one, two or three of a conducting, semi-conducting, or non-conducting (insulator) material; or to nanoparticles such as metal (e.g. gold, silver or selenium) or metal oxide (e.g. iron oxide or titanium oxide) nanoparticles; or to polymers and nanotubes. More specifically the material is not particularly limited and may be selected from the group consisting of metals, metal alloys, metal compounds (including metal oxides), carbon, glass beads, silica, and silicon wafers. The metal of said metal or metal oxide may be selected, without limitation, from the group consisting of gold, silver, nickel, iron and titanium. When the material is carbon it may be present in any form, including nanotubes.

The term "ultra-thin" layer refers to layers whose thicknesses do not exceed twice the height of the grafted (thia) calix[n]arene. The term "height" in this context refers to the distance between the surface that is grafted and the part of the grafted (thia)calix[n]arene molecule that is furthest away from the surface, not including substituents introduced during an optional post-functionalization step. Or put alternatively, ultra-thin layers will have a thickness of at maximum two (thia)calix[n]arene molecules. Usually the ultra-thin layer has a thickness from about 1 nm to 4 nm, or from about 1.2 nm to about 3.2 nm.

The terms "rather dense" and "dense" are used to describe a surface of a material that is coated with molecules in such way that molecules considered as single spheres or cylinders occupy an area equivalent to more than 50%, or more than 60%, or more than 70%, of a close-packed organization of the spheres or cylinders according to the compact Van der Vaals model.

The term "semiconductor" refers to materials with electrical conductivity intermediate in magnitude between that of a conductor and an insulator. This means a conductivity of about $10^3$ to about $10^{-8}$ siemens per centimeter. Examples of semiconductors include graphite, silicon, germanium, arsenic, selenium and tellurium, and mixtures such as gallium arsenide, and silicon carbide SiC, SiOC (grafting using diazonium salts on inorganic dielectrics, SiC, or SiOC, has been described in EP 1948720-A) or SiO$_2$, inorganic dielectrics, organic semiconductors, PPF, graphene, highly ordered pyrolytic graphite (HOPG) and carbon nanotubes semiconducting.

The term "conductor" refers to materials with electrical conductivity above $10^3$ siemens per centimeter. Examples of conductors include, but are not limited to, metals and metal alloys, e.g. carbon, iron, ruthenium, osmium, copper, silver, gold, zinc, cadmium, mercury, aluminum, and metal alloys such as bronze, brass. Good results can be obtained with carbon, copper, silver, iron, gold and platinum.

Non-conducting materials refers to materials with a conductivity below $10^{-8}$ siemens per centimeter. Examples include, but are not limited to, glass (e.g. glass beads or glass plates), paper, polymers (e.g. polypropylene, polyethylene, polystyrene or polylactic acid) or pigments (e.g. titanium oxide nanoparticles).

The term "halo" is generic to fluoro, chloro, bromo, or iodo. The term "halide" refers to fluoride, chloride, bromide, or iodide.

As used herein A$^-$ represents an inorganic or organic anion, such as a BF$_4^-$, or a halide anion, in particular a chloride anion.

The term "alkyl" refers to non-aromatic hydrocarbon groups. In particular "alkyl" refers to linear or branched, cyclic (e.g. C$_{3-10}$ cycloalkyl) and non-cyclic (acyclic) hydrocarbon groups. These may be unsaturated (see "alkenyl" and "alkynyl" below) or, preferably, saturated. They can have varying numbers of carbon atoms, e.g. up to about 30, or up to about 20, or up to about 15, or up to about 10 carbon atoms. Alkyl groups thus include C$_{1-30}$ alkyl, C$_{1-10}$ alkyl (as more specifically defined below), C$_{1-6}$ alkyl, or C$_{1-4}$ alkyl groups.

The term "$C_{1-10}$ alkyl" denotes straight and branched saturated hydrocarbon radicals having from one to ten carbon atoms such as, for example, methyl, ethyl, 1-propyl, 2-propyl, 1-butyl, 2-butyl, 2-methylpropyl, 1-pentyl, 2-pentyl, 2-methylpropyl, 1-hexyl and other hexyl isomers, 1-heptyl and other heptyl isomers, 1-octyl and other octyl isomers, 1-nonyl and other nonyl isomers, 1-decyl and other decyl isomers. The term "$C_{1-6}$ alkyl" include one to six carbon atoms. "$C_{1-4}$alkyl" have from one to four carbon atoms. Of particular interest are straight (non-branched) $C_{1-10}$alkyl, $C_{1-6}$alkyl, or $C_{1-4}$alkyl groups.

With "alkenyl" there is meant an alkyl group, as specified herein, with one or more, in particular with one, double bond. Of particular interest amongst these are allyl and vinyl. Likewise, "alkynyl" refers to an alkyl group, as specified herein, with one or more, in particular with one, triple bond. Of interest amongst these are ethynyl and propynyl "$C_1$-$C_{30}$alkoxy" or "$C_1$-$C_6$alkoxy" or "$C_1$-$C_4$alkoxy" refers to straight and branched saturated alkoxy groups having from one to thirty, or one to six, or one to four, carbon atoms such as methoxy, ethoxy, propoxy, isopropoxy, butoxy, isobutoxy, t-butoxy, pentoxy, isopentoxy, hexoxy, isohexoxy, and the like.

The terms "carboxylic acid" or "carboxyl" refer to a group of formula —COOH. The terms "carboxylic acid ester" or "thioester" in particular refers to a group —COOR' or respectively —COSR', wherein each R' is as specified herein.

The terms "azido" or "azide" refer to a —$N_3$ group.

The terms "amido" or "amide" are meant to include unsubstituted and substituted amide groups; in particular these terms may refer to a group —CO—NR'R", wherein R' and R" each independently represent hydrogen, benzyl, or alkyl (the latter in particular being, $C_1$-$C_{30}$alkyl, $C_1$-$C_{10}$alkyl, or $C_1$-$C_6$alkyl, or $C_1$-$C_4$alkyl), any of these alkyls being optionally substituted. In one embodiment said alkyl may be substituted with one, two, three, or more, substituents selected from $CF_3$, carboxylic acid, $C_1$-$C_6$alkoxycarbonyl, ethenyl, ethynyl, cyanide, acyl chloride, an alkyl (e.g. $C_1$-$C_{30}$ alkyl) or benzyl thioester, urea, alkyl (e.g. $C_1$-$C_{30}$ alkyl) or benzyl urea, hydroxyl, and mercapto. Of interest is —CONR'R", wherein R" is hydrogen. Also of interest is —CONR'R", wherein R' and R" are the same, and in particular are hydrogen, alkyl (e.g. $C_1$-$C_{30}$ alkyl, $C_1$-$C_{10}$ alkyl, $C_1$-$C_6$ alkyl, or $C_1$-$C_4$ alkyl), or benzyl.

The terms "amino" or "amine" are meant to include unsubstituted and substituted amine groups; in particular these terms may refer to a group NR'R", wherein R' and R" are as specified herein.

The terms "imino" or "imine" are meant to include unsubstituted and substituted imine groups; in particular these terms may refer to a group —C=NR', wherein R' is as specified herein.

The term "substituted disulfide" in particular refers to a disulfide —S—S—R''', wherein R''' has the same meaning as R', as defined herein, except that it is not hydrogen.

The term "carbamate" is meant to include unsubstituted and substituted carbamate groups; in particular this term may refer to a group —NH—CO—OR''', wherein R''' is as defined herein.

The terms "ureido" and "thioureido" are meant to include unsubstituted and substituted ureido and thioureido groups; in particular these terms may refer to a group —NH—CO—NR'R" or respectively —NH—CS—NR'R", wherein R' and R" are as specified herein.

The terms "phosphino" or "phosphine" are meant to include unsubstituted and substituted phosphine groups; in particular these terms may refer to a group —PR'R", wherein R' and R" are as specified herein. Similarly, "phosphinoxy" or "phosphine oxide" refer to a group —P(=O)R'R".

Any heterocyclic moiety, including those specifically mentioned herein, may be substituted with one or more, in particular with one, two, or three, substituents. The latter may be the same as the substituents (other than heterocyclyl) on $R^1$, $R^2$, etc., being alkyl.

Amino acids include the 20 natural amino acids and chemical (non-naturally occurring) analogues thereof. Amino acid derivatives include esters, N—, O— and S-alkylated derivatives, and the like.

As used herein with respect to a substituting group, and unless otherwise stated, the term "aryl" designate any mono- or polycyclic aromatic monovalent hydrocarbon group having from 6 up to 30 carbon atoms such as but not limited to phenyl, naphthyl, anthracenyl, phenantracyl, fluoranthenyl, chrysenyl, pyrenyl, biphenylyl, terphenyl, picenyl, indenyl, biphenyl, indacenyl, benzocyclobutenyl, benzocyclooctenyl and the like, including fused benzo-$C_{4-8}$ cycloalkyl groups such as, for instance, indanyl, tetrahydronaphtyl, fluorenyl and the like, all of the said groups being optionally substituted with one or more substituents independently selected from the group consisting of halogen, trifluoromethyl, $C_{1-4}$ alkyl, cyano and nitro, such as for instance 4-fluorophenyl, 4-chlorophenyl, 3,4-dichlorophenyl, 4-cyanophenyl, 2,6-dichlorophenyl, 2-fluorophenyl, 3-chlorophenyl, 3,5-dichlorophenyl and the like.

As used herein and unless otherwise stated, the term "stereoisomer" refers to all possible different isomeric as well as conformational forms which the compounds of structural formula may possess, in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

As used herein with respect to a substituting group, and unless otherwise stated, the term "heterocyclic" mean a mono- or polycyclic, saturated or mono-unsaturated or poly-unsaturated monovalent hydrocarbon radical having from 2 up to 15 carbon atoms and including one or more heteroatoms in one or more heterocyclic rings, each of said rings having from 3 to 10 atoms (and optionally further including one or more heteroatoms attached to one or more carbon atoms of said ring, for instance in the form of a carbonyl or thiocarbonyl or selenocarbonyl group, and/or to one or more heteroatoms of said ring, for instance in the form of a sulfone, sulfoxide, N-oxide, phosphate, phosphonate or selenium oxide group), each of said heteroatoms being independently selected from the group consisting of nitrogen, oxygen, sulfur, selenium and phosphorus, also including radicals wherein a heterocyclic ring is fused to one or more aromatic hydrocarbon rings for instance in the form of benzo-fused, dibenzo-fused and naphtho-fused heterocyclic radicals; within this definition are included heterocyclic radicals such as, but not limited to, diazepinyl, oxadiazinyl, thiadiazinyl, dithiazinyl, triazolonyl, diazepinonyl, triazepinyl, tiazepinonyl, tetrazepinonyl, benzoquinolinyl, benzothiazinyl, benzothiazinonyl, benzoxa-thiinyl, benzodioxinyl, benzodithiinyl, benzoxazepinyl, benzothiazepinyl, benzodiazepinyl, benzodioxepinyl, benzodithiepinyl, benzoxazocinyl, benzothiazocinyl, benzodiazocinyl, benzoxathiocinyl, benzodioxocinyl, benzotrioxepinyl, benzoxathiazepinyl, benzoxa-diazepinyl, benzothiadiazepinyl, benzotriazepinyl, benzoxathiepinyl, benzotriazinonyl, benzoxazolinonyl, azetidinonyl, azaspiroundecyl, dithiaspirodecyl, selenazinyl, selen-azolyl, selenophenyl, hypoxanthinyl, azahypo-xanthinyl, bipyrazinyl, bipyridinyl, oxazolidinyl, diselenopyrimidinyl, benzodioxocinyl, benzopyrenyl, benzopyranonyl, benzophenazinyl, benzoquinolizinyl, dibenzocarbazolyl, dibenzoacridinyl, dibenzo-phenazinyl, dibenzothiepinyl, dibenzoxepinyl, dibenzopyranonyl, dibenzoquinoxalinyl, dibenzothiazepinyl, dibenzisoquinolinyl, tetraazaadamantyl, thiatetraazaadamantyl, oxauracil, oxazinyl, dibenzothiophenyl, dibenzofuranyl, oxazolinyl, oxazolonyl, azaindolyl, azolonyl, thiazolinyl, thiazolonyl, thiazolidinyl, thiazanyl, pyrimidonyl, thiopyrimidonyl, thiamorpholinyl, azlactonyl, naphthindazolyl, naphthindolyl, naphthothiazolyl, naphthothioxolyl, naphthoxindolyl, naphthotriazolyl, naphthopyranyl, oxabicycloheptyl, azabenzimidazolyl, azacycloheptyl, azacyclooctyl, azacyclononyl, azabicyclononyl, tetrahydrofuiyl, tetrahydropyranyl, tetrahydropyronyl, tetrahydroquinoleinyl, tetrahydro-thienyl and dioxide thereof, dihydrothienyl dioxide, dioxindolyl, dioxinyl, dioxenyl, dioxazinyl, thioxanyl, thioxolyl, thiourazolyl, thiohiazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoxazinyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl (benzothiofuranyl), phenopyronyl, phenoxazolyl, pyridinyl, dihydropyridinyl, tetrahydropyridinyl, piperidinyl, morpholinyl, thiomorpholinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofuryl, furoyl, hydantoinyl, dioxolanyl, dioxolyl, dithianyl, dithienyl, dithiinyl, thienyl, indolyl, indazolyl, benzofuryl, quinolyl, quinazolinyl, quinoxalinyl, carbazolyl, phenoxazinyl, phenothiazinyl, xanthenyl, purinyl, benzothienyl, naphthothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteiidinyl, carbolinyl, acridinyl, peiimidinyl, phenanthrolinyl, phenazinyl, phenothiazinyl, hnidazolinyl, imidazolidinyl, benzimidazolyl, pyrazolinyl, pyrazolidinyl, pyrrolinyl, pyrroli-dinyl, piperazinyl, uridinyl, thymidinyl, cytidinyl, azirinyl, aziridinyl, diazirinyl, diaziridinyl, oxiranyl, oxazhidinyl, dioxiranyl, thiiranyl, azetyl, dihydroazetyl, azetidinyl, oxetyl, oxetanyl, oxetanonyl, homopiperazinyl, homopiperidinyl, thietyl, thietanyl, diazabicyclooctyl, diazetyl, diaziridinonyl, diaziridinethionyl, chromanyl, chromanonyl, thiochromanyl, thiochromanonyl, thiochromenyl, benzofuranyl, benzisothiazolyl, benzocarbazolyl, benzochromonyl, benzisoalloxazinyl, benzocoumarinyl, thiocoumarinyl, phenometoxazinyl, phenoparoxazinyl, phentriazinyl, thiodiazinyl, thiodiazolyl, indoxyl, thioindoxyl, benzodiazinyl (e.g. phthalazinyl), phthalidyl, phthalimidinyl, phthalazonyl, alloxazinyl, dibenzopyronyl (i.e. xanthonyl), xanthionyl, isatyl, isopyrazolyl, isopyrazolonyl, urazolyl, urazinyl, uretinyl, uretidinyl, succinyl, succinimido, benzylsultimyl, benzylsultamyl and the like, including all possible isomeric forms thereof, wherein each carbon atom of said heterocyclic ring may furthermore be independently substituted with a substituent selected from the group consisting of halogen, nitro, $C_{1-7}$ alkyl (optionally containing one or more functions or radicals selected from the group consisting of carbonyl (oxo), alcohol (hydroxyl), ether (alkoxy), acetal, amino, imino, oximino, alkyloximino, amino-acid, cyano, carboxylic acid ester or amide, nitro, thio alkyl, thio $C_{3-10}$ cycloalkyl, $C_{1-7}$ alkylamino, cycloalkylamino, alkenylamino, cycloalkenylamino, alkynylamino, acylamino, arylalkyl-amino, hydroxylalkylamino, mercaptoalkylamino, heterocyclic-substituted alkylamino, heterocyclic amino, heterocyclic-substituted arylamino, hydrazino, alkylhydrazino, phenylhydrazino, sulfonyl, sulfonamido and halogen), $C_{3-7}$ alkenyl, $C_{2-7}$ alkynyl, halo $C_{1-7}$ alkyl, $C_{3-10}$ cycloalkyl, aryl, arylalkyl, alkylaryl, alkylacyl, arylacyl, hydroxyl, amino, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic-substituted alkylamino, heterocyclic amino, heterocyclic-substituted arylamino, hydrazino, alkylhydrazino, phenylhydrazino, sulfhydryl, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxylamino, cyano, carboxylic acid or esters or thioesters or amides thereof, thiocarboxylic acid or esters or thioesters or amides thereof; depending upon the number of unsaturations in the 3 to 10 atoms ring, heterocyclic radicals may be sub-divided into heteroaromatic (or "heteroaryl") radicals and non-aromatic heterocyclic radicals; when a heteroatom of said non-aromatic heterocyclic radical is nitrogen, the latter may be substituted with a substituent selected from the group consisting of $C_{1-7}$ alkyl, $C_{3-10}$ cycloalkyl, aryl, arylalkyl and alkylaryl.

A calixarene as a substituent on $R^1$, $R^2$, etc., being alkyl, may be a (thia)calix[n]arene as specified herein.

A cyclodextrin in particular is an α-, β-, or γ-cyclodextrin, linked through one of its hydroxyl groups.

In the embodiments where two or more of $R^1$, $R^2$, $R^3$, $R^4$, $R^5$ and $R^6$ form a bridge (bridging group) selected from phosphine, phosphine oxide, amino, imino, amido, ureido, thioureido, ester, thioester, alkene, alkyne or alkyl, one of the hydrogen atoms or substituents on these moieties are replaced by a bond. In particular in this instance, where applicable, R', R", or R'" may be a bond.

The indicator "0.1" at the right bracket of the phenyl moieties bearing $R^5$ and $R^6$ means that the latter is absent or present. Of interest are the (thia)calix[n]arenes wherein these two indicators are 0, i.e. the (thia)calix[4]arenes.

Whenever mention is made to particular (thia)calix[n]arenes or particular substitution patterns, or both, such as in the various embodiments mentioned herein, the term "(thia)calix[n]arene" or its plural refer to (thia)calix[n]arene moieties grafted on the surface of a material, or to the (thia)calix[n]arenes described herein, e.g. the (thia)calix[n]arenes of formula I, II, III, IV, V, or VI.

One embodiment concerns (thia)calix[4]arenes, (thia)calix[5]arenes, or (thia)calix[6]arenes, wherein $R^2$, $R^3$, and $R^4$ and, if present, $R^5$ and $R^6$ have the same meaning while $R^1$ has a different meaning.

Another embodiment concerns (thia)calix[4]arenes, (thia)calix[5]arenes, or (thia)calix[6]arenes, wherein all of $R^1$, $R^2$, $R^3$, $R^4$, and if present $R^5$ and $R^6$, have the same meaning.

In another embodiment, one, two, three, four, if possible, five or six of $R^1$, $R^2$, $R^3$, $R^4$ and, if present, $R^5$ and $R^6$, each independently are hydrogen or $C_1$-$C_{30}$ alkyl, the latter being optionally substituted with 1, 2, or 3 of the substituents mentioned herein.

The $C_1$-$C_{30}$ alkyl group in $R^1$, $R^2$, $R^3$, $R^4$, $R^5$ and $R^6$ may be $C_1$-$C_{10}$ alkyl $C_1$-$C_6$alkyl or $C_1$-$C_4$alkyl; or in particular said group may be —$CH_2$—, —$(CH_2)_2$—, —$(CH_2)_3$—, or —$(CH_2)_4$—. The latter four may be linked to hydrogen or to one of the substituents of said $C_1$-$C_{30}$ alkyl. Or, in particular, the latter four may be linked to $CF_3$, carboxyl, or to $C_1$-$C_4$alkoxycarbonyl.

In a particular embodiment, one, two, three, four, if possible, five or six of $R^1$, $R^2$, $R^3$, $R^4$ and, if present, $R^5$ and $R^6$ are n-propyl, —$CH_2$—COOH, —$CH_2$—COO$C_1$-$C_4$alkyl, or —$(CH_2)_3$—$CF_3$.

In a further embodiment, one, two, or three of $R^1$, $R^2$, $R^3$, $R^4$ and, if present, $R^5$ and $R^6$, are $C_1$-$C_{30}$ alkyl, optionally substituted as specified herein, and the others are hydrogen.

In another embodiment, one of $R^1$, $R^2$, $R^3$, $R^4$ and, if present, $R^5$ and $R^6$ is hydrogen, and the others are $C_1$-$C_{30}$ alkyl, optionally substituted as specified herein.

A particular embodiment concerns calix[4]arenes, wherein all $R^1$, $R^2$, $R^3$, and $R^4$ are independently selected from —$(CH_2)$—COOH, $(C_1$-$C_4$alkoxycarbonyl)-$CH_2$—, —$(CH_2)_3$—$CF_3$, and —$(CH_2)_3$—H. Or in this embodiment, one of $R^1$, $R^2$, $R^3$, and $R^4$ is selected from hydrogen, —$(CH_2)$—COOH, or $(C_1$-$C_4$alkoxy-carbonyl)-$CH_2$—, and the others are —$(CH_2)_3$—$CF_3$ or —$(CH_2)_3$—H.

In one embodiment, one, two, three, four, or if possible, five or six of $R^1$, $R^2$, $R^3$, and $R^4$ and, if present, $R^5$ and $R^6$ is $C_1$-$C_{30}$ alkyl substituted with one substituent as specified herein, which substituent in particular may be a carboxylic acid group, a carboxylic acid derivative (e.g. $C_1$-$C_4$alkoxycarbonyl), —CO—NR'R", ethynyl, —$N_3$, —OH, —NR'R", or a carbamate group, wherein R' and R" are as specified herein As specified herein, $Y^1$—, $Y^2$—, $Y^3$—, $Y^4$— and $Y^5$— each independently represent a covalent link with the material's surface, or $Y^1$—, $Y^2$—, $Y^3$—, $Y^4$— and $Y^5$— each independently represent OH, hydrogen, $NO_2$, halogen, $C_{1-30}$ alkyl, acyle, carboxylic acid and derivatives thereof (e.g. ester, amide), —$N_3$, alkenyl or alkynyl. This means that one, two, three, or if present, four, or five of $Y^1$—, $Y^2$—, $Y^3$—, $Y^4$— and $Y^5$— can be a covalent link, while the others are OH, hydrogen, $NO_2$, halogen, $C_{1-30}$ alkyle, acyle, carboxylic acid and derivatives thereof (e.g. ester, amide), —$N_3$, alkenyl or alkynyl.

In one embodiment all of $Y^1$, $Y^2$, $Y^3$, and if present, $Y^4$ and $Y^5$ are the same. In a further embodiment, in the compounds of formula II, all of $Y^1$, $Y^2$, $Y^3$, and if present $Y^4$ and $Y^5$, are amino.

In a further embodiment, in the compounds of formula III, all of $Y^1$, $Y^2$, $Y^3$, and if present $Y^4$ and $Y^5$, are nitro.

A further embodiment concerns calix[4]arenes, calix[5]arenes, or calix[6]arenes, i.e. the
calix[n]arenes wherein X is methylene. Another embodiment concerns thiacalix[4]arenes, thiacalix[5]arenes, or thiacalix[6]arenes, i.e. the (thia)calix[n]arenes wherein X is —S—.

Of interest are the (thia)calix[4]arenes, in particular the calix[4]arenes.

A particular embodiment concerns calix[4]arenes, wherein all $R^1$, $R^2$, $R^3$, and $R^4$ are selected from —$(CH_2)$—COOH, $(C_1$-$C_4$alkoxycarbonyl)-$CH_2$—, —$(CH_2)_3$—$CF_3$, and —$(CH_2)_3$—H. Or one of $R^1$, $R^2$, $R^3$, and $R^4$ is selected from hydrogen, —$(CH_2)$—COOH, or $(C_1$-$C_4$alkoxy-carbonyl)-$CH_2$—, and the others are —$(CH_2)_3$—$CF_3$ or —$(CH_2)_3$—H.

The (thia)calix[n]arene moieties may be grafted through only one linkage (or bond), i.e. $Y^1$—, $Y^2$—, $Y^3$—, and if present $Y^4$— and $Y^5$— are all other than a bond. This may be preferred for (thia)calix[n]arenes wherein n is 5 or 6.

In another embodiment, the (thia)calix[n]arene of formula I bears two, three or, if applicable, five or six diazonium groups, and an equal number of bonds are formed with the surface of the material. This may be applicable for the less flexible (thia)calix[n]arenes, in particular where n is 4, or with appropriately substituted (thia)calix[n]arenes. This may also be applicable for the more flexible (thia)calix[n]arenes, such as the (thia)calix[5]arenes or the (thia)calix[6]arenes which can be modified by adding appropriate substituents on the small rim or covalent bridges between the phenolic moieties (i.e. where two or more of $R^1$, $R^2$, $R^3$, $R^4$, $R^5$ and $R^6$ are covalently linked either directly or through a bridge as defined above).

The skilled person will be able to select the number of bonds to the surface per calixarene moiety based on the conformational flexibility of the (thia)calix[n]arene moiety, or on the possibilities in terms of chemical configuration, in particular as regards sterical hindrance.

The diazonium salts of formula I can be linked to the surface by an electrochemical, chemical, or thermal reaction.

In case of an electrochemical reaction, the diazonium salts are in solution containing the material to be grafted as cathode. This preparation involves (i) the in situ (or ex-situ) transformation of calix[n]-anilines into calix[4]-diazonium salts and (ii) a subsequent covalent anchoring of these diazonium salts on the surface upon electrochemical reduction. The electrochemical reduction can be performed by using different electrochemical techniques such as voltammetry, chronopotentiometry, chronoamperometry or by pulsed techniques.

In case of a chemical reaction, the diazonium salts are activated using a reducing agent such as, but not limited to, sodium borohydride, hypophosphorous acid, ferrocenemethanol, iron powder or catalytic amounts of a iodide.

In case of a thermal reaction, the decomposition of the diazonium salts leading to the formation of radical species to be bound onto surface can be achieved by art-known methodology such as by heating at 60-70° C. in water or in acetonitrile, either with aryldiazonium salts in solution or with in situ generation of the diazonium salt with an alkyl nitrite.

Without being bound by theory, it is assumed that the diazonium salts are reduced to produce aryl radicals, which form links with the surface of the conducting or semiconducting or non conducting material.

Different diazonium salts of formula I can be used in the same grafting procedure in order to lead a combined layer.

The diazonium salts of formula I can be prepared by reacting the (thia)calix[n]-anilines of formula II with a nitrite such as sodium nitrite, in an aqueous acidic solution or with an alkyl nitrite such as isoamylnitrite or tertio-butylnitrite in an organic solvent (e.g. dichloromethane, polar aprotic solvents such as acetonitrile, dimethylformamide, dimethylacetamide, and the like solvents) or with nitoso salt (NOK$^-$) in organic solvents (e.g. acetonitrile). The diazonium salts of formula I, preferably the $BF_4^-$ salts, can be prepared from an ice-cold solution of the corresponding anilines in $HBF_4$ by the slow addition of $NaNO_2$ (in excess) dissolved in a minimum amount of water. The precipitate is filtered off, washed with $H_2O$. The diazonium salts of formula I, preferably the $BF_4^-$ salts, can be prepared from a solution of the corresponding anilines in acetonitrile in the presence of $NOBF_4$ (preferably in a slight molar excess) at low temperature (e.g. −40° C.). The crude residue is then washed with diethylether and ethanol. The diazonium salts of formula I can be prepared in situ from the corresponding (thia)calix[n]-anilines of formula II in the presence of the material to be grafted.

The (thia)calix[n]-anilines of formula II in turn can be prepared from the corresponding p-nitro-(thia)calix[n]arenes of formula III by a reduction reaction:

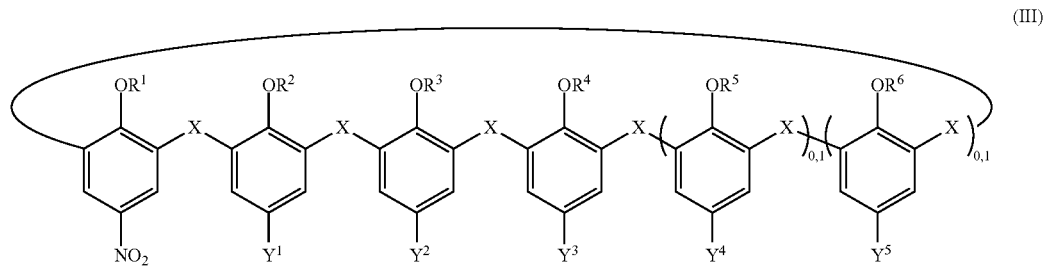

(III)

The reduction reaction may, for example, comprise reacting the p-nitro-(thia)calix[n]arenes of formula III with hydrazine in the presence of a palladium catalyst such as Pd on carbon, in ethanol at increased temperatures such as the reflux temperature of the reaction mixture.

In the p-tbutyl-(thia)calix[n]arenes of formula V, $Y^1$, $Y^2$, $Y^3$, $Y^4$ and $Y^5$ each independently represent $C_{1-30}$ alkyl (in particular p-tbutyl), OH, H, halogen, $C_{1-30}$ alkyl, acyl, carboxylic acid and derivatives thereof (e.g. ester, amide), —$N_3$, alkenyl or alkynyl. In one embodiment, all of $Y^1$, $Y^2$, $Y^3$, and if present, $Y^4$ and $Y^5$ are p-tbutyl.

The p-nitro-(thia)calix[n]arenes of formula III can be prepared from the corresponding p-tbutyl-(thia)calix[n]arenes of formula IV:

reaction-inert solvent, e.g. a halogenated hydrocarbon such as dichloromethane.

In the p-tbutyl-(thia)calix[n]arenes of formula IV, X, $R^1$, $R^2$, $R^3$, $R^4$, and if present, $R^5$ and $R^6$ are as defined herein; $Y^1$, $Y^2$, $Y^3$, $Y^4$ and $Y^5$ each independently represent p-tbutyl, OH, H, halogen, $C_{1-30}$ alkyl, acyl, carboxylic acid and derivatives thereof (e.g. ester, amide), —$N_3$, alkenyl or alkynyl. In one embodiment, all of $Y^1$, $Y^2$, $Y^3$, and if present, $Y^4$ and $Y^5$ are p-tbutyl.

The corresponding p-tbutyl-(thia)calix[n]arenes of formula IV, wherein all of $R^1$, $R^2$, $R^3$, $R^4$, and if present, $R^5$ and $R^6$ are an alkyl or substituted alkyl groups, can be prepared by alkylating p-tbutyl-(thia)calix[n]arenes of formula V

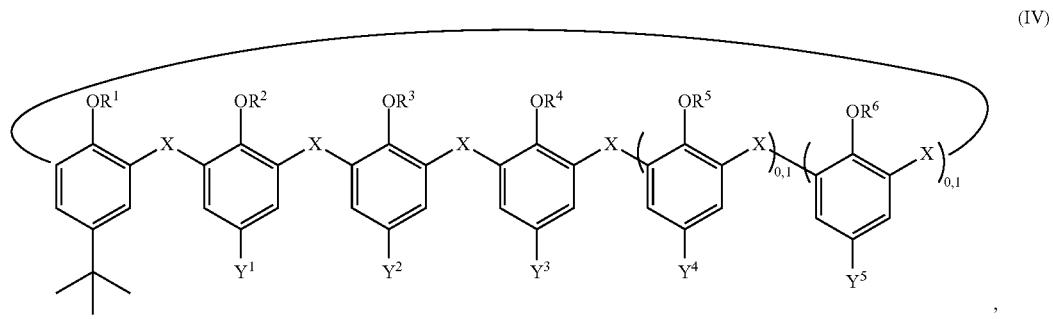

(IV)

by the reaction of (IV) with fuming nitric acid in glacial acetic acid, preferably in a 1:1 (v/v) ratio, in a suitable having a hydroxyl group in the 1-position of the phenyl moieties:

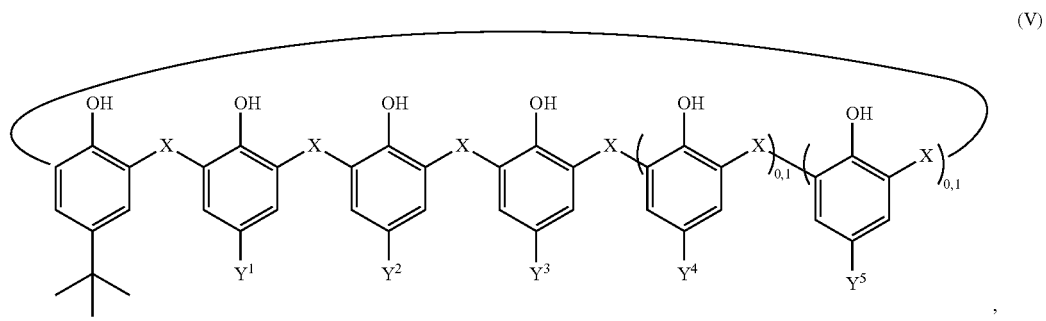

(V)

with an alkylating agent of formula $R^1$-Lg, wherein Lg represents a leaving group, in particular a halo group other than fluoro, e.g. chloro or bromo or iodo. This reaction can be conducted in the presence either of a weak (e.g. barium hydroxide/barium oxide mixture) or a strong base (e.g. a hydride such as NaH). Suitable solvents for this reaction include THF and the dipolar aprotic solvents, in particular DMF. When using an appropriate base and an appropriate number of equivalents of $R^1$-Lg, monosubstituted, disubstituted, trisubstituted, or tetrasubstituted p-tbutyl-(thia)calix[n]arenes can be obtained. These in turn can be reacted with one or more alkylating agents represented by the structural formula $R^2$-Lg, or $R^3$-Lg, or $R^4$-Lg, thus preparing compounds of formula (IV) wherein $R^1$, $R^2$, $R^3$, $R^4$, and, if present, $R^5$ and $R^6$ have different meanings. A stronger base such as an alkali metal hydride such as NaH, in an aprotic solvent, is preferably used in the latter procedure.

When $R^1$, $R^2$, $R^3$, $R^4$, and, if present, $R^5$ and $R^6$ are acyclic $C_{1-30}$ alkyl substituted with a group which may interfere, or compete, with the desired alkylation reaction of the compound (V), such as but not limited to, carboxylic acid, —OH, amino, amido, imino, carbamate, acyl chloride, ureido, thioureido, amino-acid or peptido, it may be best to proceed in more than one step. For instance an amino group may be protected with an amino-protecting group before the alkylation reaction and afterwards the amino-protecting group may be cleaved off. With respect to a carboxylic acid or acid amide, the alkylation reaction may be carried out with an alkylating agent having a non-interfering carboxylic acid ester, followed by hydrolysis and optionally amidation. Depending upon the type and likelihood of interference of the substituent with the desired alkylation reaction, the person skilled in the art of organic chemistry will be able to appropriately select the synthetic strategy, i.e. the type and conditions of additional steps, in order to overcome this difficulty.

Suitable examples of alkylating agents wherein $R^1$, $R^2$, $R^3$, $R^4$, and, if present, $R^5$ and $R^6$ are unsubstituted acyclic $C_{1-30}$ alkyl include, but are nor limited to, 1-bromoethane, 1-bromopropane, 1-bromobutane, 1-bromo-2-methylpropane, 1-bromopentane, 1-bromo-2-methylbutane, 1-bromohexane, 1-bromoheptane, 1-bromooctane, 1-bromodecane, 1-bromododecane, 1-bromohexadecane (cetyl bromide), 1-bromooctadecane (stearyl bromide), 1-chloroethane, 1-chloropropane, 1-chlorobutane, 1-chloro-2-methylpropane, 1-chloropentane, 1-chloro-2-methylbutane, 1-chlorohexane, 1-chloroheptane, 1-chlorooctane, 1-chlorodecane, 1-chlorododecane, 1-chlorohexadecane (cetyl chloride), 1-bromooctadecane (stearyl chloride), 1-iodoethane, 1-iodopropane, 1-iodobutane, 1-iodo-2-methylpropane, 1-iodopentane, 1-iodo-2-methylbutane, 1-iodohexane, 1-iodoheptane, 1-iodooctane, 1-iododecane, 1-iodododecane, 1-iodohexadecane (cetyl iodide), and 1-iodooctadecane (stearyl iodide).

Suitable examples of alkylating agents wherein $R^1$, $R^2$, $R^3$, $R^4$, and, if present, $R^5$ and $R^6$ are unsubstituted partly or fully cyclic $C_{3-30}$ alkyl include, but are nor limited to, iodocyclohexane, bromocyclohexane, chlorocyclohexane, bromocyclopentane, bromocyclobutane, chlorocyclopropane, (bromomethyl)cyclobutane, (bromomethyl)cyclopentane, (bromomethyl)cyclohexane, (2-bromoethyl)cyclohexane, and (bromomethyl)cyclooctane.

Suitable examples of alkylating agents wherein $R^1$, $R^2$, $R^3$, $R^4$, and, if present, $R^5$ and $R^6$ are acyclic $C_{1-30}$ alkyl substituted with one or more, e.g. two or three, fluoro include, but are not limited to, 1-fluoro-2-iodoethane, 1-bromo-2-fluoroethane, 1-iodo-3-fluoropropane, 1-bromo-1,3-difluoropropane, 1-bromo-3,3,3-trifluoropropane, 1-iodo-4,4,4-trifluorobutane, 1-bromo-4,4,4-trifluorobutane, and 6-bromo-1,1,1-trifluorohexane.

Suitable examples of alkylating agents wherein $R^1$, $R^2$, $R^3$, $R^4$, and, if present, $R^5$ and $R^6$ are acyclic $C_{1-30}$ alkyl substituted with one or more $C_{1-30}$ alkoxy include, but are nor limited to, 1-bromo-6-methoxyhexane, 1-bromo-6-ethoxyhexane, 1-bromo-5-methoxypentane, 1-bromo-6-ethoxypentane, 1-bromo-4-methoxybutane, 1-bromo-4-ethoxybutane, 1-bromo-3-methoxypropane, 1-bromo-3-ethoxypropane, 1-bromo-2-methoxyethane, 1-bromo-2-ethoxyethane, and 1-bromo-2-(2-methoxyethoxy)ethane. Suitable examples of alkylating agents wherein $R^1$, $R^2$, $R^3$, $R^4$, and, if present, $R^5$ and $R^6$ are acyclic $C_{1-30}$ alkyl substituted with one or more alkenyl include, but are not limited to, allyl chloride, allyl bromide, and allyl iodide.

Suitable examples of alkylating agents wherein $R^1$, $R^2$, $R^3$, $R^4$, and, if present, $R^5$ and $R^6$ are acyclic $C_{1-30}$ alkyl substituted with one or more alkynyl include, but are not limited to, propargyl chloride and propargyl bromide.

Suitable examples of alkylating agents wherein $R^1$, $R^2$, $R^3$, $R^4$, and, if present, $R^5$ and $R^6$ are acyclic $C_{1-30}$ alkyl substituted with one or more cyano include, but are not limited to, 1-bromo-3-cyanopropane and 1-chloro-3-cyanopropane.

Suitable examples of alkylating agents wherein $R^1$, $R^2$, $R^3$, $R^4$, and, if present, $R^5$ and $R^6$ are acyclic $C_{1-30}$ alkyl substituted with one or more aryl or substituted aryl (wherein the one or more substituents of the aryl group are independently selected from the group consisting of fluoro, cyano, $C_{1-30}$ alkyl and $C_{1-30}$ alkoxy) include, but are not limited to, benzyl bromide, 2-methylbenzyl bromide, 4-tert-butylbenzyl chloride, 4-tert-butylbenzyl bromide, 3,5-di-tert-butylbenzyl bromide, benzyl chloride, benzyl iodide, 4-fluorobenzyl chloride, 3-fluorobenzyl chloride, 2-fluorobenzyl chloride, 4-cyanobenzyl chloride, 3-cyanobenzyl chloride, 2-cyanobenzyl chloride, 4-cyanobenzyl bromide, 3-cyanobenzyl bromide, 2-cyanobenzyl bromide, 4-fluorobenzyl bromide, 3-fluorobenzyl bromide, 2-fluorobenzyl bromide, 4-methoxybenzyl chloride, 3-methoxybenzyl chloride, 2-methoxybenzyl chloride, 4-ethoxybenzyl chloride, 4-isopropoxybenzyl chloride, 3-methoxybenzyl bromide and 4-methoxybenzyl bromide.

Suitable examples of alkylating agents wherein $R^1$, $R^2$, $R^3$, $R^4$, and, if present, $R^5$ and $R^6$ are acyclic $C_{1-30}$ alkyl substituted with one or more heterocyclic groups include those wherein the heterocyclic group is saturated, partly unsaturated or fully unsaturated (aromatic) and has from 3 to 7 ring members and wherein the ring includes one, two or three heteroatoms independently selected from the group consisting of nitrogen, oxygen and sulfur. Representative examples of alkylating agents wherein $R^1$, $R^2$, $R^3$, $R^4$, and, if present, $R^5$ and $R^6$ are acyclic $C_{1-30}$ alkyl substituted with one or more heteroaromatic groups include, but are not limited to, 2-(bromomethyl)furan, 2-(bromomethyl)-5-(trifluoro-methyl)furan, 3-(bromomethyl)pyridine, 4-(bromomethyl)pyridine, 2-(bromomethyl)thiophene, 3-(bromomethyl)thiophene and 2-(chloromethyl)thiazole. Representative examples of alkylating agents wherein $R^1$, $R^2$, $R^3$, $R^4$, and, if present, $R^5$ and $R^6$ are acyclic $C_{1-30}$ alkyl substituted with one or more saturated heterocyclic groups include 3-(bromomethyl)piperidine (optionally N-protected), 2-(chloromethyl)-1,3-dioxolane, and 4-benzyl-3-chloromethyl-morpholine.

Suitable examples of alkylating agents wherein $R^1$, $R^2$, $R^3$, $R^4$, and, if present, $R^5$ and $R^6$ are acyclic $C_{1-30}$ alkyl substituted with one or more carboxylic acid esters include, but are not limited to, ethyl bromoacetate, ethyl chloroacetate, methyl bromoacetate, methyl chloroacetate, ethyl 3-bromopropionate, methyl 3-bromopropionate, ethyl 3-chloropropionate, methyl 3-chloropropionate, ethyl 4-chlorobutyrate, methyl 4-chlorobutyrate, ethyl 4-bromobutyrate, methyl 4-bromobutyrate, ethyl 6-bromohexanoate, methyl 6-bromohexanoate, ethyl 6-chlorohexanoate, and methyl 6-chlorohexanoate.

In particular, the above method can be used to introduce —$CH_2COOR$ groups (R=$C_{1-30}$ alkyl), which can then be hydrolyzed to the corresponding —$CH_2COOH$ substituted (thia)calix[n]arenes, using a strong base such as a tetraalkyl ammonium hydroxide. The latter can be converted to the corresponding p-nitro-acetic acid substituted (thia)calix[n]arenes, which upon a nitro-to-amino reduction yield the corresponding (thia)calix[n]anilines. The latter procedure may involve the conversion of the p-nitro-acetic acid substituted (thia)calix[n]arenes to the tin(II) salts, which also act as reductant.

The p-tbutyl-(thia)calix[n]arenes of formula IV, wherein all of $R^1$, $R^2$, $R^3$, $R^4$, and if present, $R^5$ and $R^6$ are all hydrogen can be alkylated with an alkyl halide as defined hereinabove in the presence of a strong base such as e.g. a hydride such as NaH in an aprotic solvent such as THF.

(Thia)calix[n]arenes wherein X is S, can be converted to the corresponding sulfoxides by controlled oxidation with a peroxide, or to the corresponding sulfones with ample amounts of oxidant.

Alkylation of p-tbutyl-(thia)calix[n]arenes of formula IV can lead to partially alkylated derivatives, whose hydroxyl groups can in turn be alkylated with a different alkyl group.

In the p-tbutyl-(thia)calix[n]arenes of formula V, $Y^1$, $Y^2$, $Y^3$, $Y^4$ and $Y^5$ each independently represent $C_{1-30}$ alkyl (in particular p-tbutyl), OH, H, halogen, $C_{1-30}$ alkyl, acyl, carboxylic acid and derivatives thereof (e.g. ester, amide), —$N_3$, alkenyl or alkynyl. In one embodiment, all of $Y^1$, $Y^2$, $Y^3$, and if present, $Y^4$ and $Y^5$ are p-tbutyl.

The compounds of formula (V) having four, five or six phenolic moieties, i.e. 4-tert-butyl-calix[4]arene, 4-tert-butyl-calix[5]arene, 4-tert-butyl-calix[6]arene, 4-tert-butylsulfonylcalix[4]arene, 4-tert-butyl-thiacalix[4]arene are known compounds and are commercially available.

Thiacalix[n]arenes that are known include thiacalix[4]arene tetra-O-propyl, thiacalix[4]arene tetra-O-propyl tetra$NO_2$, thiacalix[4]arene tetra-O-ester and O-acid. Known calix[n]arenes include calix[5]arene penta-O-propyl, calix[5]arene penta-O-ester and O-acid, calix[5]arene penta-O-acid penta-$NO_2$, calix[6]arene hexa-O-propyl, calix[6]arene hexa-O-propyl hexa-$NO_2$, calix[6]arene hexa-O-ester, calix[6]arene hexa-O-acid, calix[6]arene hexa-O-acid hexa-$NO_2$.

Some of the known (thia)calix[n]arenes can be used as starting materials or can be converted into compounds of formula III, IV or V using art-known methodology or any of the methodology described herein.

Direct links or bridging groups between the substituents $R^1$, $R^2$, $R^3$, $R^4$, $R^5$ and $R^6$ may be introduced in the (thia)calix[n]arene intermediates or by post-functionalization using art-known methodology.

After linkage to the surface of a material, the immobilized (thia)calix[n]arenes can be further functionalized ("post-functionalized") through the anchoring of various chemical species such as molecules, biomolecules, nanoparticles, polymers or oligomers. The $R^1$, $R^2$, $R^3$, $R^4$ and, if present, $R^5$ and $R^6$ groups can be linked to the various chemical species, or can be first chemically modified, e.g. by converting carboxyl groups into amido or ester groups or vice versa.

The materials grafted with the thus obtained materials can be conveniently post-functionalized, e.g. by converting the carboxyl groups into amido or ester groups.

The ultra-thin layer of grafted (thia)calix[n]arenes is a highly regular monolayer and does not present the large ramifications typically encountered with other systems, which lead to a complex and irregular surface coating. The grafted (thia)calix[n]arenes may form a rather dense coating, so that little free surface of the coated material is present.

The grafted (thia)calix[n]arene monolayer, when functionalized with a carboxylic acid group can be esterified or converted with an appropriate amine into amides. Appropriate amines include not only simple amines but also amino acids, peptides, proteins and various chemical species (such as ligands for metal ions or for anions, molecular receptors, oligomers or polymers) with one or multiple appending amino arms. The carboxylic acid group can further be linked to hydroxyl-containing species such as saccharides, cyclodextrins and polyethylene glycols.

The covalent surface grafting of functionalized (thia)calix[n]arenes (with e.g. COOH or alkyne groups on the small rim) on the large rim provides well-organized and compact monolayers, which can be post-functionalized. In other words, grafted (thia)calix[n]arenes induce a pre-structuration and a pre-functionalization of the surface at the molecular level.

The grafted materials of the invention can be used as a versatile platform for further modification, in particular the anchoring of further molecules resulting a regular and possibly rather dense molecular layer of various chemical species (molecules, nanoparticles, biomolecules, ligands for metal ions or anions, molecular receptors, oligomers or polymers, etc.) on conducting or semiconducting or non conducting material surfaces.

The following examples are solely meant to illustrate various embodiments of the present invention and should not be construed as a limitation of its scope.

Calix[5]arenes and calix[6]arenes, as well as thiacalix[n]arenes can be prepared following the same or similar procedures as described in the following examples, which describe calix[4]arene derivatives.

Example 1—Synthesis and Characterization of calix[4]arene tris-O-propyl 59

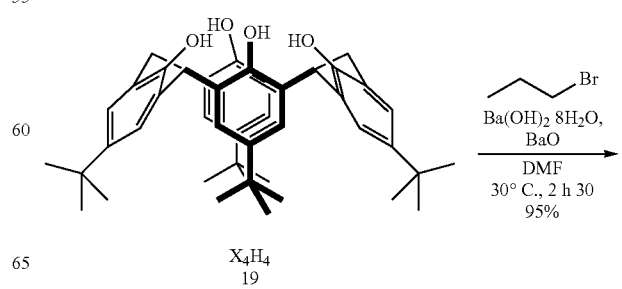

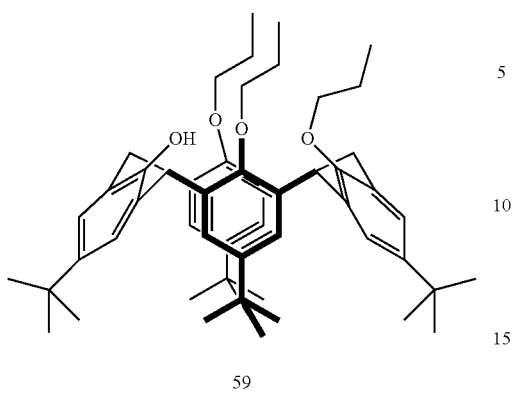

59 p-tbutyl-calix[4]arene, X₄H₄ 19 (5.01 g, 7.72 mmol, 1 equiv.), Ba(OH)₂.8H₂O (7.42 g, 0.0235 mol, 3 equiv.) and BaO (5.54 g, 0.0361 mol, 4.7 equiv.) were suspended in DMF (190 mL). 1-bromopropane (35 mL, 0.385 mol, 50 equiv.) was added and the reaction mixture was stirred for 2 h30 at 30° C. under inert atmosphere. The mixture reaction was concentrated under reduced pressure and dissolved in CH₂Cl₂ (300 mL). The organic layer was washed with H₂O (4×200 mL) and combined aqueous layers were extracted with CH₂Cl₂ (2×250 mL). The combined organic layers were concentrated under reduced pressure to yield compound 59 as a white solid (5.6645 g, 7.31 mmol, 95%) which was characterized as follows:

¹H NMR (300 MHz, CDCl₃, 298K): δ (ppm)=0.82 (s, 18H, tBu), 0.95 (t, ³J=7.5 Hz, 3H, CH₂CH₃), 1.09 (t, ³J=7.4 Hz, 6H, CH₂CH₃), 1.32 (s, 9H, tBu), 1.34 (s, 9H, tBu), 1.81-2.01 (mult, 4H, CH₂CH₃), 2.33 (mult, 2H, CH₂CH₃), 3.16 (d, ²J=12.6 Hz, 2H, ArCH₂ eq), 3.22 (d, ²J=13.2 Hz, 2H, ArCH₂ eq), 3.75 (t, ³J=7.3 Hz, 4H, OCH₂), 3.84 (t, ³J=8.4 Hz, 2H, OCH₂), 4.31-4.39 (m, 4H, ArCH₂ ax), 5.58 (s, 1H, OH), 6.49-6.53 (m, 4H, ArH), 7.05 (s, 2H, ArH), 7.13 (s, 2H, ArH).

Example 2—Synthesis and Characterization of calix[4]arene tetra-O-n-propyl 60

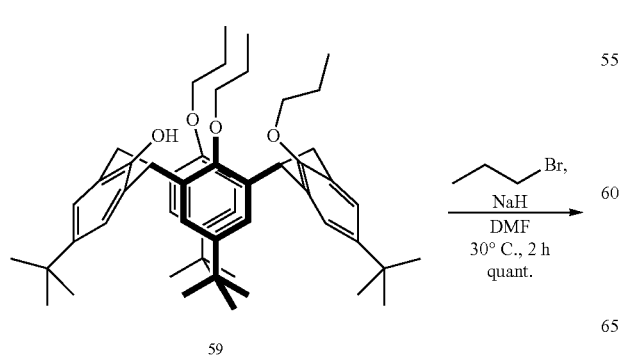

59

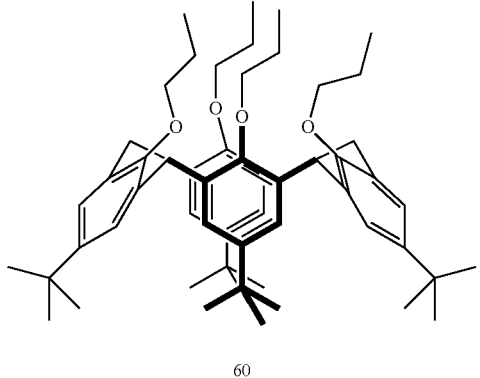

60

Calix[4]arene tris-O-propyl 59 (0.506 g, 0.653 mmol, 1 equiv.) and NaH (60% in oil, 0.154 g, 3.85 mmol, 6 equiv.) were suspended in DMF (20 mL). 1-bromopropane (1.2 mL, 0.0132 mol, 20 equiv.) was added and the mixture reaction was stirred for 2 h at 30° C. under inert atmosphere. The mixture reaction was concentrated under reduced pressure and dissolved in CH₂Cl₂ (50 mL). The organic layer was washed with H₂O (3×20 mL) and combined aqueous layers were extracted with CH₂Cl₂ (2×30 mL). The combined organic layers were concentrated under reduced pressure to yield compound 60 as a white solid (0.548 g, 0.653 mmol, 100%) which was characterized as follows:

¹H NMR (300 MHz, CDCl₃, 298K): δ (ppm)=1.02 (t, ³J=7.5 Hz, 12H, CH₂CH₃), 1.10 (s, 36H, tBu), 2.05 (mult, 8H, CH₂CH₃), 3.13 (d, ²J=14.0 Hz, 4H, ArCH₂ eq), 3.84 (t, ³J=7.8 Hz, 8H, OCH₂), 4.44 (d, ²J=12.6 Hz, 4H, ArCH₂ ax), 6.80 (s, 8H, ArH).

Example 3—Synthesis and Characterization of calix[4]arene tetra-O-n-propyl tetra-NO₂ 61

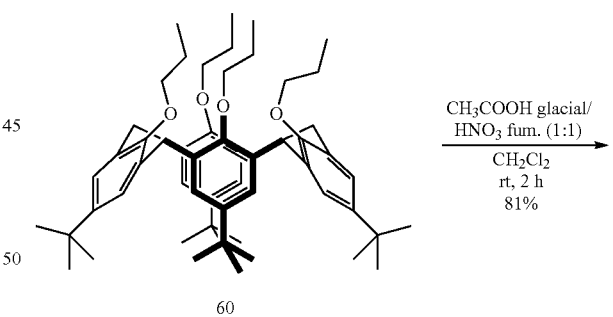

60

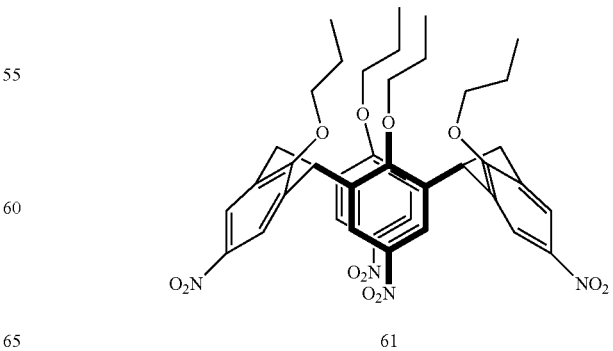

61

Calix[4]arene tetra-O-n-propyl 60 (0.554 g, 0.677 mmol, 1 equiv.) was dissolved in $CH_2Cl_2$ (25 mL). A mixture of glacial $CH_3COOH$/fuming $HNO_3$ (1:1) (5.6 mL) was added at 0° C. and the reaction mixture was stirred for 2 hours at room temperature to yield a purple solution which turned to yellow. The reaction mixture was concentrated under reduced pressure and dissolved in $CH_2Cl_2$ (50 mL). The organic layer was washed with $H_2O$ (3×20 mL) and combined aqueous layers were extracted with $CH_2Cl_2$ (2×30 mL). The combined organic layers were concentrated under reduced pressure and the crude residue was washed with MeOH (2×2 mL) to yield compound 61 as a yellow solid (0.425 g, 0.549 mmol, 81%) which was characterized as follows:

$^1$H NMR (300 MHz, $CDCl_3$, 298K): δ (ppm)=1.02 (t, $^3J$=7.5 Hz, 12H, $CH_2CH_3$), 1.91 (mult, 8H, $CH_2CH_3$), 3.40 (d, $^2J$=14.1 Hz, 4H, $ArCH_2$ eq), 3.96 (t, $^3J$=7.5 Hz, 8H, $OCH_2$), 4.53 (d, $^2J$=13.8 Hz, 4H, $ArCH_2$ ax), 7.57 (s, 8H, ArH).

Example 4—Synthesis and Characterization of calix[4]arene tetra-O-n-propyl tetra-NH$_2$ 62

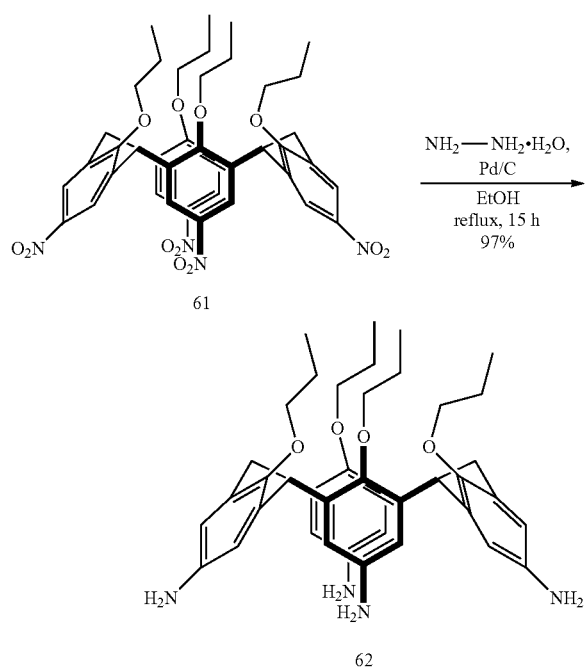

Calix[4]arene tetra-O-n-propyl tetra-NO$_2$ 61 (0.405 g, 0.524 mmol, 1 equiv.) and Pd/C (0.041 g, 0.385 mmol, 0.75 equiv.) were suspended in EtOH (15 mL). Hydrazine hydrate (2.4 mL, 0.494 mol, 94 equiv.) was added and the reaction mixture was stirred for 15 hours at reflux. The reaction mixture was filtered on Celite and the Celite was washed with EtOH and $CH_2Cl_2$. The filtrate was concentrated under reduced pressure to yield compound 62 as a yellow solid (0.332 g, 0.509 mmol, 97%) which was characterized as follows:

$^1$H NMR (300 MHz, $CDCl_3$, 298K): δ (ppm)=0.95 (t, $^3J$=7.5 Hz, 12H, $CH_2CH_3$), 1.84 (mult, 8H, $CH_2CH_3$), 2.92 (d, $^2J$=13.2 Hz, 4H, $ArCH_2$ eq), 3.72 (t, $^3J$=7.5 Hz, 8H, $OCH_2$), 4.31 (d, $^2J$=13.2 Hz, 4H, $ArCH_2$ ax), 6.06 (s, 8H, ArH).

Example 5—Synthesis and Characterization of calix[4]arene tris-O-butyl-F$_3$ 63

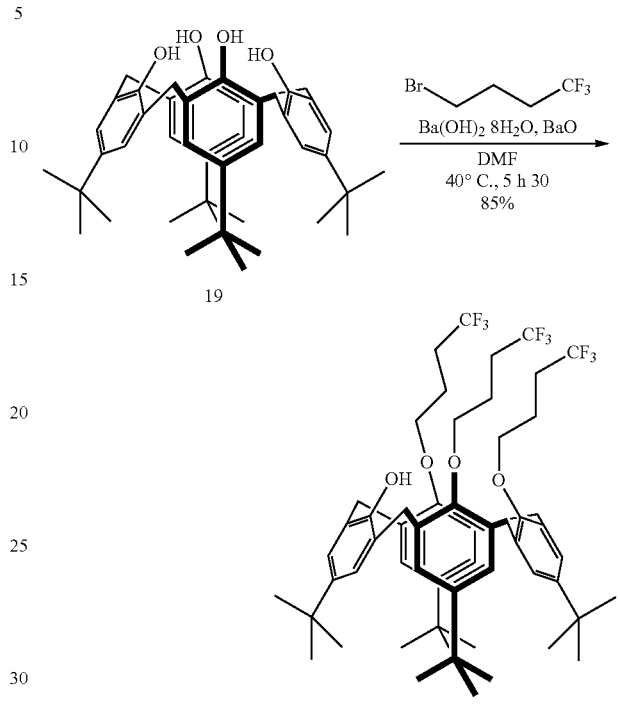

p-tbutyl-calix[4]arene, $X_4H_4$ 19 (0.501 g, 0.771 mmol, 1 equiv.), $Ba(OH)_2 \cdot 8H_2O$ (0.761 g, 2.41 mmol, 3 equiv.) and BaO (0.703 g, 5.09 mmol, 6.6 equiv.) were suspended in DMF (20 mL). 1-Bromo-4,4,4-trifluorobutane (0.550 mL, 4.48 mmol, 6 equiv.) was added and the reaction mixture was stirred for 5 h30 at 40° C. under inert atmosphere. The reaction mixture was concentrated under reduced pressure and dissolved in $CH_2Cl_2$ (50 mL). The organic layer was washed with $H_2O$ (3×25 mL) and combined aqueous layers were extracted with $CH_2Cl_2$ (2×35 mL). The combined organic layers were concentrated under reduced pressure. The crude residue was purified by flash chromatography ($C_6H_{12}/CH_2Cl_2$ 8:2) to yield compound 63 as a white solid (0.639 g, 0.653 mmol, 85%) which was characterized as follows:

Rf=0.27 ($C_6H_{12}/CH_2Cl_2$ 8:2);
m.p. 82° C.;
IR(cm$^{-1}$): 3281, 2967, 1484, 1255, 1154, 1024, 874;
$^1$H NMR (400 MHz, $CDCl_3$, 298K): δ (ppm)=0.82 (s, 18H, tBu), 1.34 (s, 9H, tBu), 1.35 (s, 9H, tBu), 2.12 (mult, 4H, $CH_2CH_2CF_3$), 2.25-2.44 (m, 6H, $CH_2CF_3$), 2.51 (mult, 2H, $CH_2CH_2CF_3$), 3.23 (d, $^2J$=12.8 Hz, 2H, $ArCH_2$ eq) 3.27 (d, $^2J$=13.2 Hz, 2H, $ArCH_2$ eq), 3.87 (mult, 4H, $OCH_2$), 3.96 (t, $^3J$=10.8 Hz, 2H, OCH2), 4.21-4.30 (m, 4H, $ArCH_2$ax), 5.12 (s, 1H, OH), 6.49-6.54 (m, 4H, ArH), 7.08 (s, 2H, ArH), 7.17 (s, 2H, ArH);
$^{13}$C NMR (75 MHz, $CDCl_3$, 298K): δ (ppm)=22.6, 22.9, 30.5, 30.9, 31.1 (2C), 31.3, 31.8, 31.9, 33.8, 34.0, 34.3, 73.0, 74.4, 125.0, 125.2 (2C), 125.3, 125.7, 126.1, 128.6 (q, $^1J$=279 Hz), 129.5 (q, $^1J$=272 Hz), 131.6, 131.9, 142.2, 145.8, 146.5, 150.6, 151.2, 153.4;
HRMS (ESI-TOF) calculated for $C_{56}H_{71}O_4F_9$ (M+Na)$^+$ 1001.5106. found 1001.5145

Example 6—Synthesis and Characterization of calix[4]arene tetra-O-butyl-F₃ 64

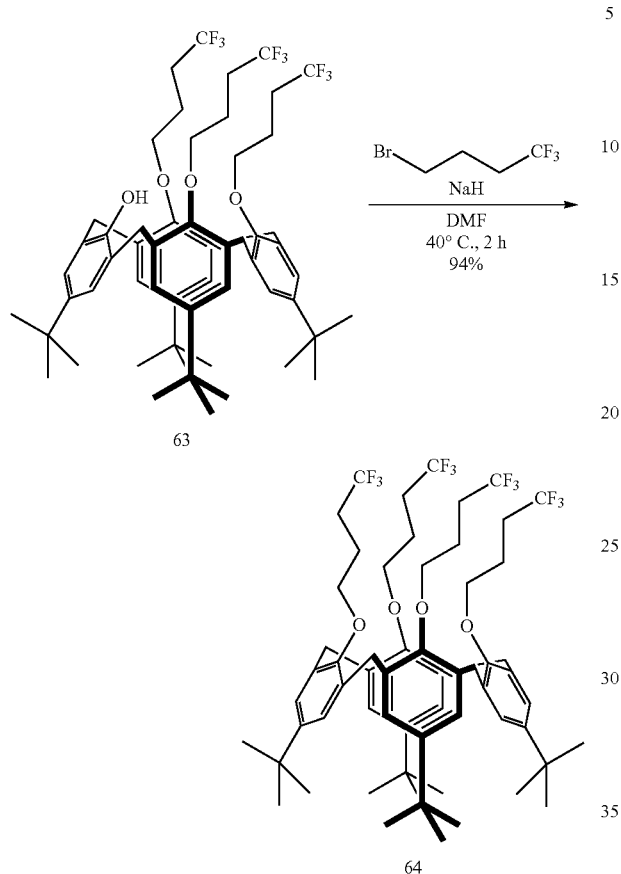

Example 7—Synthesis and Characterization of calix[4]arene tetra-O-butyl-F₃ tetra-NO₂ 65

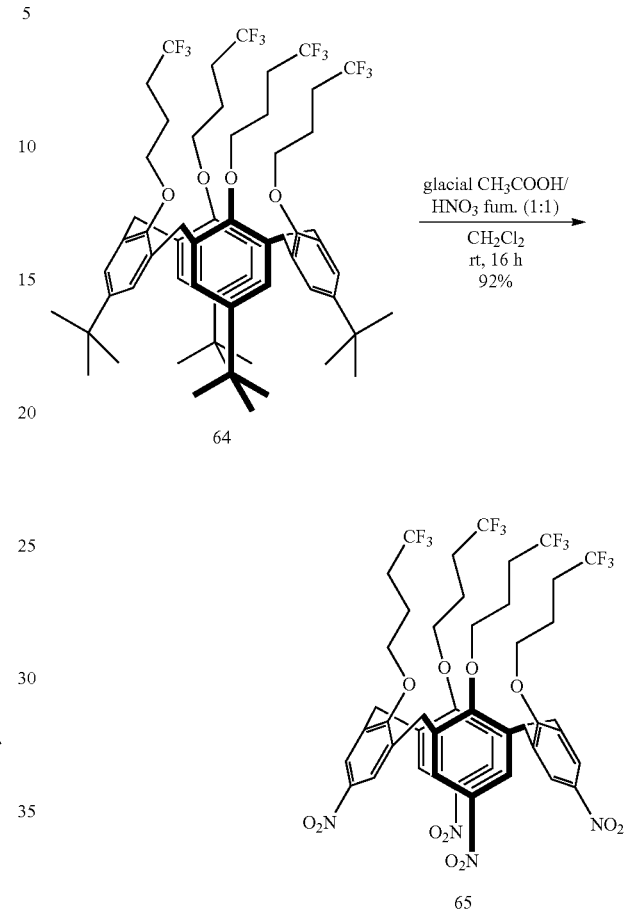

Calix[4]arene tris-O-butyl-F₃ 63 (0.639 g, 0.653 mmol, 1 equiv.) and NaH (60% in oil, 0.162 g, 4.05 mmol, 6 equiv.) were suspended in DMF (20 mL). 1-Bromo-4,4,4-trifluorobutane (0.162 mL, 1.31 mmol, 2 equiv.) was added and the reaction mixture was stirred for 2 hours at 40° C. under inert atmosphere. The reaction mixture was concentrated under reduced pressure and dissolved in $CH_2Cl_2$ (75 mL). The organic layer was washed with $H_2O$ (3×40 mL) and combined aqueous layers were extracted with $CH_2Cl_2$ (2×60 mL). The combined organic layers were concentrated under reduced pressure. The crude residue was purified by flash chromatography ($C_6H_{12}/CH_2Cl_2$ 9:1) to yield compound 64 as a white solid (0.667 g, 0.612 mmol, 94%) which was characterized as follows:

Rf=0.32 ($C_6H_{12}/CH_2Cl_2$ 9:1);
m.p. 197° C.;
IR($cm^{-1}$): 3298, 2966, 1482, 1292, 1257, 1155, 1030, 867;
$^1$H NMR (300 MHz, $CDCl_3$, 298K): δ (ppm)=1.08 (s, 36H, tBu), 2.19-2.22 (m, 16H, $CH_2CH_2CF_3$), 3.18 (d, $^2J$=12.6 Hz, 4H, $ArCH_2$ eq), 3.89 (tb, $^3J$=6.9 Hz, 8H, $OCH_2$), 4.28 (d, $^2J$=12.6 Hz, 4H, $ArCH_2$ ax), 6.80 (s, 8H, ArH);
$^{13}$C NMR (75 MHz, $CDCl_3$, 298K): δ (ppm)=23.0, 30.8, 31.1, 31.5, 34.0, 73.7, 125.4, 127.2 (q, $^1J$=276 Hz), 133.6, 142.3, 152.9;
HRMS (ESI-TOF) calculated for $C_{60}H_{76}O_4F_{12}$ (M+Na)⁺ 1111,5450. found 1111,5453.

Calix[4]arene tetra-O-butylCF₃ 64 (0.538 g, 0.494 mmol, 1 equiv.) was dissolved in $CH_2Cl_2$ (27 mL). A mixture of glacial $CH_3COOH$/fuming $HNO_3$ (1:1) (5.4 mL) was added and the reaction mixture was stirred for 16 hours at room temperature. The reaction mixture was concentrated under reduced pressure and dissolved in $CH_2Cl_2$ (50 mL). The organic layer was washed with $H_2O$ (3×25 mL) and combined aqueous layers were extracted with $CH_2Cl_2$ (2×30 mL). The combined organic layers were concentrated under reduced pressure. The crude residue was washed with MeOH (2×2 mL) to yield compound 65 as a yellow solid (0.475 g, 0.455 mmol, 92%) which was characterized as follows:

m.p. 350-352° C. (decomposition);
IR($cm^{-1}$): 3411, 2962, 1526, 1353, 1257, 1151, 1030, 841;
$^1$H NMR (300 MHz, $CD_3CN$, 298K): δ (ppm)=2.15-2.29 (m, 16H, $CH_2CH_2CF_3$), 3.58 (d, $^2J$=14.1 Hz, 4H, $ArCH_2$ eq), 4.06 (t, $^3J$=7.2 Hz, 8H, $OCH_2$), 4.43 (d, $^2J$=14.1 Hz, 4H, $ArCH_2$ ax), 7.64 (s, 8H, ArH);
13C NMR (75 MHz, $CD_3CN$, 298K): δ (ppm)=23.5, 30.9, 31.4, 75.2, 125.1, 127.5* (q, $^1J$=276 Hz), 136.9, 144.1, 162.1.

*This value was determined by HMBC

Example 8—Synthesis and Characterization of calix[4]arene tetra-O-butyl-F₃ tetra-NH₂ 66

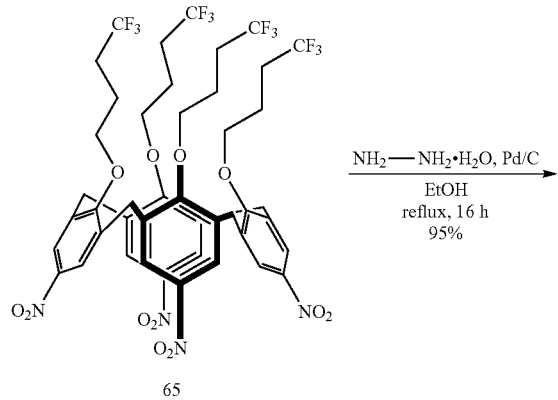

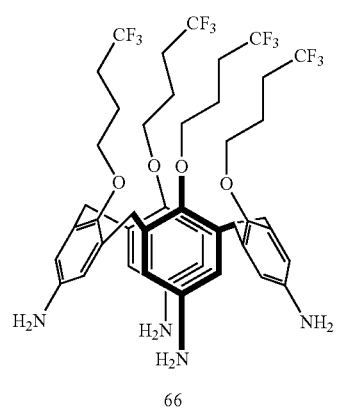

Calix[4]arene tetra-O-butyl-F₃ tetra-NO₂ 65 (0.400 g, 0.383 mmol, 1 equiv.) was suspended in EtOH (20 mL). Hydrazine hydrate (2.00 mL, 0.0411 mol, 107 equiv.) and Pd/C (0.031 g, 0.291 mmol, 0.8 equiv.) were added and the reaction mixture was stirred for 16 hours at reflux. The reaction mixture was filtered on Celite and the filtrate was concentrated under reduced pressure to yield compound 66 as a yellow solid (0.339 g, 0.366 mmol, 95%) which was characterized as follows:

m.p. 138-139° C.;

IR(cm⁻¹): 3375, 2931, 1614, 1474, 1254, 1155, 1029, 832;

¹H NMR (300 MHz, CDCl₃, 298K): δ (ppm)=2.02-2.11 (mult, 8H, CH₂CH₂CF₃), 2.12-2.24 (mult, 8H, CH₂CH₂CF₃2.97 (d, ²J=13.5 Hz, 4H, ArCH₂ eq), 3.79 (t, ³J=6.9 Hz, 8H, OCH₂), 4.17 (d, ²J=13.2 Hz, 4H, ArCH₂ ax), 6.07 (s, 8H, ArH);

¹³C NMR (75 MHz, CDCl₃, 298K): δ (ppm)=22.8, 30.6, 31.2, 73.4, 116.1, 127.2* (q, ¹J=275 Hz), 135.4, 141.1, 149.2;

HRMS (ESI-TOF) calculated for C₄₄H₄₈O₄F₁₂N₄ (M+H)⁺ 925.3562. found 925.3586.

*This value was determined by HMBC

Example 9—Synthesis and Characterization of calix[4]arene tetra-O-(ethyl acetate) 67

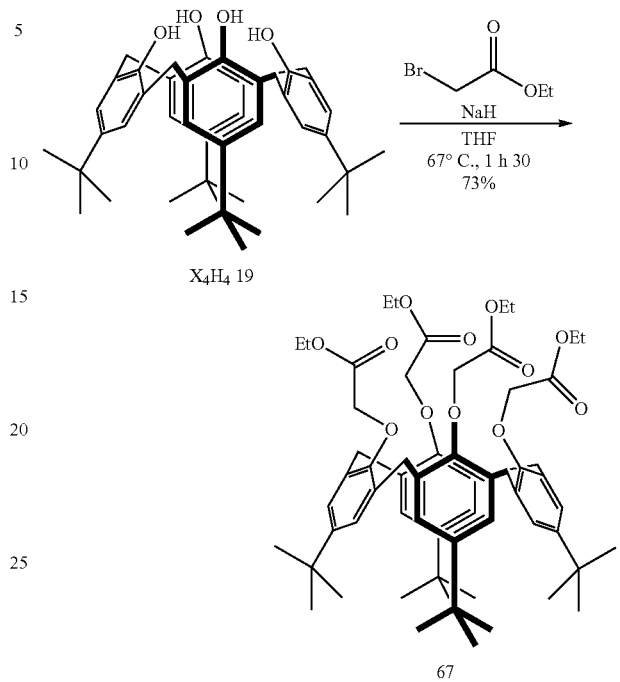

p-tbutyl-calix[4]arene, X₄H₄ 19 (1.021 g, 1.57 mmol, 1 equiv.) was dissolved in THF (40 mL). NaH (60% in oil, 0.981 g, 0.0246 mol, 16 equiv.) and ethyl bromoacetate (8.5 mL, 0.0768 mol, 49 equiv.) were added and the reaction mixture was stirred for 1 h 30 at 67° C. under inert atmosphere. EtOH (2 mL) was added to the reaction mixture which was concentrated under reduced pressure. The residue was dissolved in CH₂Cl₂ (100 mL). The organic layer was washed with H₂O (3×50 mL) and combined aqueous layers were extracted with CH₂Cl₂ (2×70 mL). The combined organic layers were concentrated under reduced pressure and the crude residue was washed with EtOH (2×4 mL) to yield compound 67 as a white solid (1.138 g, 1.15 mmol, 73%) which was characterized as follows:

¹H NMR (300 MHz, CDCl₃, 298K): δ (ppm)=1.07 (s, 36H, tBu), 1.29 (t, ³J=7.2 Hz, 12H, CH₂CH₃), 3.19 (d, ²J=14.3 Hz, 4H, ArCH₂ eq), 4.21 (q, ³J=8.0 Hz, 8H, OCH₂CH₃), 4.80 (s, 8H, OCH₂), 4.85 (d, ²J=12.9 Hz, 4H, ArCH₂ ax), 6.78 (s, 8H, ArH).

Example 10—Synthesis of calix[4]arene tetra-O-acetic acid 68

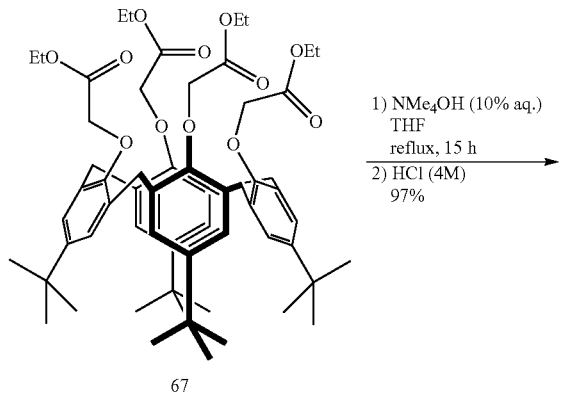

-continued

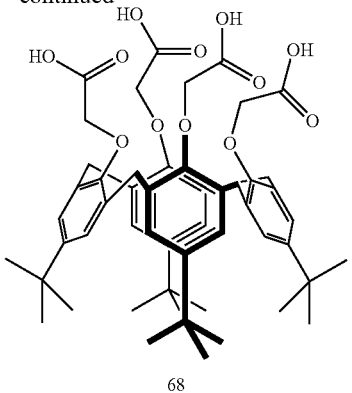

68

Calix[4]arene tetra-O-(ethyl acetate) 67 (0.719 g, 0.724 mmol, 1 equiv.) was dissolved in THF (40 mL). NMe$_4$OH (10% aq., 60 mL, 66.2 mmol, 91 equiv.) was added and the reaction mixture was stirred for 15 hours at reflux. Concentrated HCl (5 mL) was added until pH=1 and the reaction mixture was stirred for 24 hours at room temperature. THF was concentrated under reduced pressure and the precipitate was filtered. The crude residue was washed with H$_2$O (3×5 mL) to yield compound 68 as a white solid (0.617 g, 0.701 mmol, 97%) which was characterized as follows:

$^1$H NMR (300 MHz, CDCl$_3$/DMSO-d6 (1:1), 298K): δ (ppm)=1.03 (s, 36H, tBu), 3.15 (d, $^2$J=12.9 Hz, 4H, ArCH$_2$ eq), 4.57 (s, 8H, OCH$_2$), 4.78 (d, $^2$J=12.9 Hz, 4H, ArCH$_2$ ax), 6.82 (s, 8H, ArH), 12.0 (sb, 1H, COOH).

Example 11—Synthesis of calix[4]arene tetra-O-(acetic acid) tetra-NO$_2$ 69

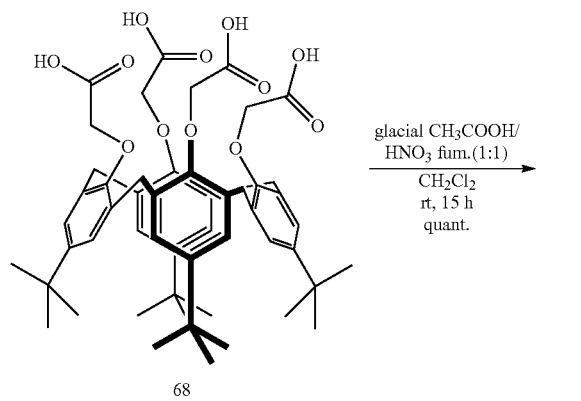

Calix[4]arene tetra-O-(acetic acid) 68 (0.565 g, 0.641 mmol, 1 equiv.) was dissolved in CH$_2$Cl$_2$ (20 mL). A mixture of glacial CH$_3$COOH/fuming HNO$_3$ (1:1) was added at 0° C. and the reaction mixture was stirred for 15 hours at room temperature. The reaction mixture was concentrated under reduced pressure. The crude residue was washed with H$_2$O (3×5 mL) to yield compound 69 (0.536 g, 0.641 mmol, 100%) which was characterized as follows:

m.p. 255-258° C. (decomposition);

IR(cm$^{-1}$): 3276, 2962, 1743, 1529, 1350, 1208, 1058;

$^1$H NMR (300 MHz, DMSO-d6, 298K): δ (ppm)=3.69 (d, $^2$J=14.7 Hz, 4H, ArCH$_2$ eq), 4.77 (s, 8H, OCH$_2$), 4.91 (d, $^2$J=13.5 Hz, 4H, ArCH$_2$ ax), 7.67 (s, 8H, ArH), 12.96 (sb, 4H, COOH).

$^{13}$C NMR (150 MHz, DMSO-d6, 298K): δ (ppm)=30.5, 70.9, 123.8, 135.6, 142.3, 161.3, 170.3.

Example 12—Synthesis and Characterization of calix[4]arene tetra-O-(acetic acid) tetra-NH$_2$ tin salt 70

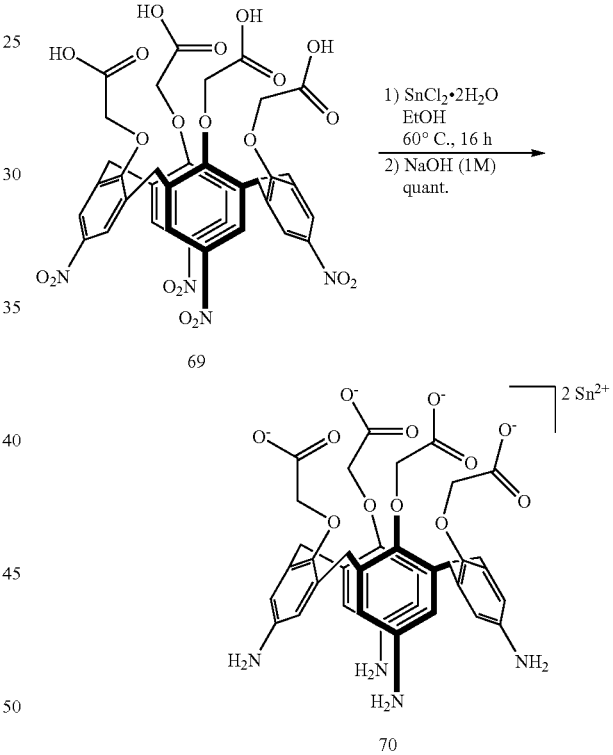

Calix[4]arene tetra-O-(acetic acid) tetra-NO$_2$ 69 (0.103 g, 0.123 mmol, 1 equiv.) was suspended in EtOH (5 mL). SnCl$_2$.2H$_2$O (0.600 g, 2.66 mmol, 22 equiv.) was added and the reaction mixture was stirred for 16 h at 60° C. under inert atmosphere. The reaction mixture was poured on H$_2$O (12 mL) at 0° C. and NaOH (1M, 10 mL) was added until pH >10. CH$_2$Cl$_2$ (30 mL) was added and the mixture was stirred for 10 minutes at 0° C. Then, the organic layer was washed with H$_2$O (2×10 mL). The combined aqueous layers were concentrated under reduced pressure and MeOH (4×0.3 mL) was added onto the residue. The filtrate was concentrated under reduced pressure to yield compound 70 (0.119 g, 0.125 mmol, 100%) which was characterized as follows:

m.p. 277° C. (decomposition);

IR(cm$^{-1}$): 3368, 2940, 1611, 1480, 1225;

$^1$H NMR (300 MHz, CD$_3$OD, 298K): δ (ppm)=3.13 (d, $^2$1=12.0 Hz, 4H, ArCH 2 eq), 4.23 (s, 8H, OCH$_2$), 4.51 (d, $^2$1=12.0 Hz, 4H, ArCH$_2$ax), 6.58 (s, 8H, ArH);

$^{13}$C NMR (75 MHz, CD$_3$OD, 298K): δ (ppm)=31.2*, 77.2*, 117.6, 137.4, 144.6, 147.2, 176.8;

HRMS (ESI-TOF) calculated for C$_{36}$H$_{36}$O$_{12}$N$_4$(M+H)$^+$ 717.2408. found 717.2403.

*This value was determined by HSQC.

Example 13—Synthesis and Characterization of calix[4]arene tris-O-propyl mono-O-(ethyl acetate) 71

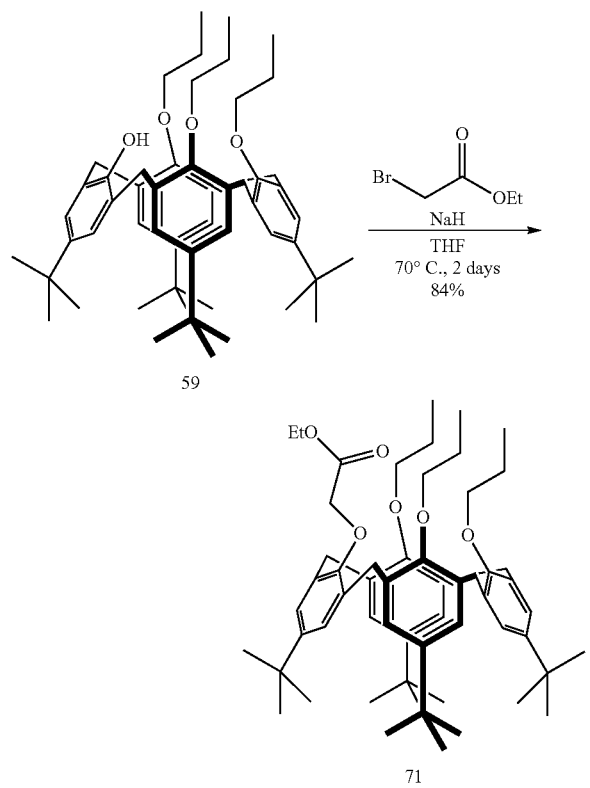

Calix[4]arene tris-O-n-propyl 59 (0.051 g, 0.0658 mmol, 1 equiv.) and NaH (60% in oil, 0.014 g, 0.350 mmol, 5.3 equiv.) were suspended in THF (1 mL) and the mixture was stirred for 15 minutes at room temperature under inert atmosphere. Ethyl bromoacetate (0.080 mL, 0.723 mmol, 11 equiv.) was added and the reaction mixture was stirred for 2 days at 70° C. under inert atmosphere. EtOH (0.5 mL) was added to stop the reaction and the mixture was concentrated under reduced pressure. The residue was dissolved in CH$_2$Cl$_2$ and the organic layer was washed with H$_2$O (3×10 mL). The combined aqueous layers were extracted with CH$_2$Cl$_2$ (2×15 mL) and the combined organic layers were concentrated under reduced pressure. The residue was purified by a washing with EtOH (2×0.4 mL) to yield compound 71 as a white solid (0.048 g, 0.0553 mmol, 84%) which was characterized as follows:

$^1$H NMR (400 MHz, CDCl$_3$, 298K): δ (ppm)=0.98-1.04 (m, 27H, tBu+CH$_2$CH$_3$), 1.17 (s, 9H, tBu), 1.18 (s, 9H, tBu), 1.30 (t, $^3$J=7.2 Hz, 3H, COCH$_2$CH$_3$), 1.97 (m, 4H, CH$_2$CH$_2$CH$_3$), 2.10 (mult, 2H, CH$_2$CH$_2$CH$_3$), 3.12 (d, $^2$J=12.4 Hz, 2H, ArCH$_2$ eq), 3.17 (d, $^2$J=12.8 Hz, 2H, ArCH$_2$ eq), 3.73-3.85 (m, 6H, OCH$_2$CH$_2$CH$_3$), 4.21 (q, $^3$J=7.2 Hz, 2H, COOCH$_2$CH$_3$), 4.41 (d, $^2$J=12.4 Hz, 2H, ArCH$_2$ ax), 4.66 (d, $^2$J=12.8 Hz, 2H, ArCH$_2$ ax), 4.83 (s, 2H, OCH$_2$CO), 6.66-6.68 (m, 4H, ArH), 6.89 (s, 2H, ArH), 6.90 (s, 2H, ArH).

Example 14—Synthesis and Characterization of calix[4]arene tris-O-n-propyl mono-O-acetic acid 72

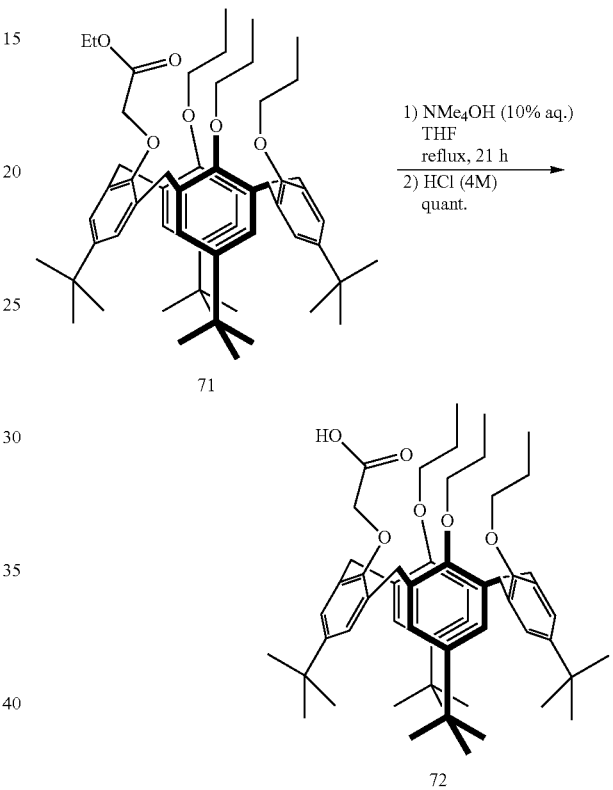

Calix[4]arene tris-O-n-propyl mono-O-(ethyl acetate) 71 (4.872 g, 5.66 mmol, 1 equiv.) was dissolved in THF (250 mL) and NMe$_4$OH (10% aq., 250 mL, 0.276 mol, 50 equiv.) was added. The reaction mixture was stirred for 21 hours at reflux under inert atmosphere. The reaction was stopped by the addition of HCl (10% aq., 50 mL) until pH=1 and the THF was removed under reduced pressure. The precipitate was filtered and washed with H$_2$O to yield compound 72 as a white solid (4.709 g, 5.65 mmol, 100%) which was characterized as follows:

m.p. 249° C.;

IR(cm$^{-1}$): 3428, 2964, 1766, 1478, 1363, 1203, 1008, 871;

$^1$H NMR (400 MHz, CDCl$_3$, 298K): δ (ppm)=0.83 (s, 18H, tBu), 0.89 (t, 3J=7.2 Hz, 3H, CH$_2$CH$_3$), 0.99 (t, 3J=7.2 Hz, 6H, CH$_2$CH$_3$), 1.32-1.37 (m, 18H, tBu), 1.83-1.97 (m, 6H, CH$_2$CH$_2$CH$_3$), 3.16 (d, $^2$J=12.8 Hz, 2H, ArCH$_2$ eq), 3.23 (d, $^2$J=13.2 Hz, 2H, ArCH$_2$ eq), 3.66-3.81 (mult, 4H, OCH$_2$CH$_2$CH$_3$), 4.01 (mult, 2H, OCH$_2$CH$_2$CH$_3$), 4.23 (d, $^2$J=12.8 Hz, 2H, ArCH$_2$ ax), 4.46 (d, $^2$J=12.4 Hz, 2H, ArCH$_2$ ax), 4.65 (s, 2H, OCH$_2$CO), 6.49 (d, 4J=2.0 Hz, 2H, ArH), 6.60 (d, 4J=2.4 Hz, 2H, ArH), 7.14 (s, 2H, ArH), 7.16 (s, 2H, ArH);

$^{13}$C NMR (75 MHz, CDCl$_3$, 298K): δ (ppm)=10.0, 10.5, 22.6, 23.3, 31.1, 31.2, 31.3, 31.7, 31.9, 33.8, 34.2, 34.4, 70.9, 77.8, 78.4, 124.7, 125.3, 125.5, 126.1, 131.7, 132.7, 135.2, 135.6, 145.0, 145.2, 147.2, 151.2, 152.0, 154.3, 170.9;

HRMS (ESI-TOF) calculated for C$_{55}$H$_{76}$O$_6$ (M+H)$^+$ 833.5720. found 833.5731.

Example 15—Synthesis and Characterization of calix[4]arene tris-O-n-propyl mono-O-(acetic acid) tetra-NO$_2$ 73

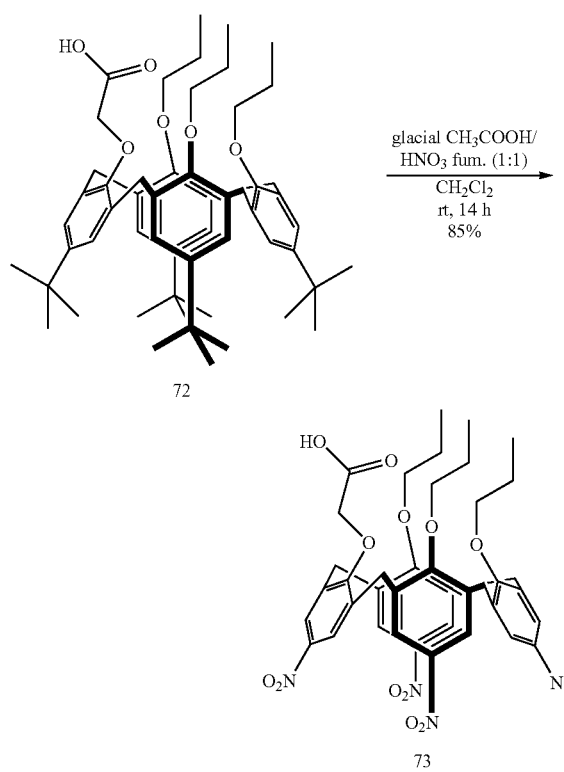

Calix[4]arene tris-O-propyl mono-O-acetic acid 72 (1.753 g, 2.10 mmol, 1 equiv.) was dissolved in CH$_2$Cl$_2$ (100 mL). A mixture of glacial CH$_3$COOH/fuming HNO$_3$ (1:1) (18 mL) was added and the reaction mixture was stirred for 14 hours at room temperature. The reaction mixture was concentrated under reduced pressure and dissolved in CH$_2$Cl$_2$ (100 mL). The organic layer was washed with H$_2$O (4×50 mL) and the combined aqueous layers were extracted with CH$_2$Cl$_2$ (1×100 mL). The combined organic layers were concentrated under reduced pressure. The crude residue was washed with EtOH (2×5 mL) to yield compound 73 as a yellow solid (1.402 g, 1.78 mmol, 85%) which was characterized as follows:

$^1$H NMR (400 MHz, CDCl$_3$, 298K): δ (ppm)=0.94 (t, $^3$J=7.6 Hz, 3H, CH$_2$CH$_3$), 1.05 (t, $^3$J=7.6 Hz, 6H, CH$_2$CH$_3$), 1.81-1.98 (m, 6H, CH$_2$CH$_2$CH$_3$), 3.45 (d, 2J=13.6 Hz, 2H, ArCH$_2$ eq), 3.54 (d, $^2$J=14.0 Hz, 2H, ArCH$_2$ eq), 3.90 (t, $^3$J=7.2 H, 4H, OCH$_2$CH$_2$CH$_3$), 4.05 (t, $^3$J=8.0 Hz, 2H, OCH$_2$CH$_2$CH$_3$), 4.53-4.60 (m, 4H, ArCH$_2$ ax), 4.88 (s, 2H, OCH$_2$CO), 7.23-7.26 (m, 4H, ArH), 8.02-8.06 (m, 4H, ArH).

Example 16—Synthesis and Characterization of calix[4]arene tris-O-n-propyl mono-O-(acetic acid)-tetra-NH$_2$ 74

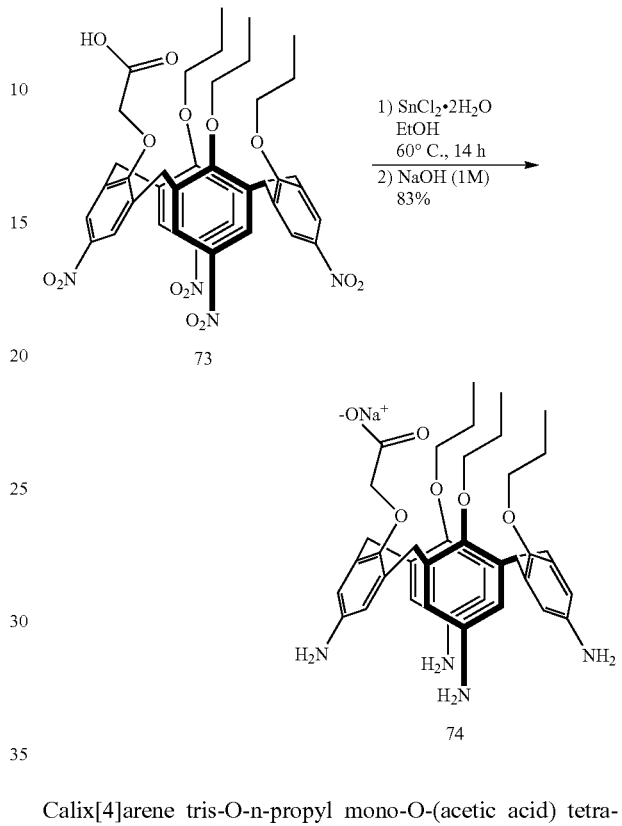

Calix[4]arene tris-O-n-propyl mono-O-(acetic acid) tetra-NO$_2$ 73 (0.401 g, 0.507 mmol, 1 equiv.) and SnCl$_2$.2H$_2$O (2.682 g, 0.0119 mol, 23 equiv.) were suspended in EtOH (20 mL). The reaction mixture was stirred at 60° C. for 14 hours. NaOH (1M, 15 mL) was added until pH >10 and the mixture was concentrated under reduced pressure. The crude residue was dissolved in MeOH (5 mL) and the precipitate was filtered. The filtrate was concentrated under reduced pressure to yield compound 74 (0.291 g, 0.422 mmol, 83%) which was characterized as follows:

m.p. 258-261° C. (decomposition);

IR(cm$^{-1}$) (KBr): 3379, 2966, 1610, 1480, 1223, 1001, 839;

$^1$H NMR (400 MHz, CD$_3$OD, 298K): δ (ppm)=0.92 (t, $^3$J=7.6 Hz, 6H, CH$_2$CH$_3$), 1.08 (t, $^3$J=7.2 Hz, 3H, CH$_2$CH$_3$), 1.79-1.98 (mult, 4H, CH$_2$CH$_2$CH$_3$), 2.03-2.13 (mult, 2H, CH$_2$CH$_2$CH$_3$), 3.16-3.25 (m, $^2$J=12.4 Hz, 4H, ArCH$_2$ eq), 3.82-3.89 (mult, 4H, OCH$_2$CH$_2$CH$_3$), 3.92-3.98 (m, 2H, OCH$_2$CH$_2$CH$_3$), 4.14 (d, $^2$J=12.4 Hz, 2H, ArCH$_2$ ax), 4.23 (s, 2H, OCH$_2$CO), 4.27 (d, $^2$J=12.4 Hz, 2H, ArCH$_2$ ax), 6.56 (d, $^4$J=2.4 Hz, 2H, ArH), 6.58 (d, $^4$J=2.4 Hz, 2H, ArH), 6.59-6.63 (m, 4H, ArH);

$^{13}$C NMR (100 MHz, CD$_3$OD, 298K): δ (ppm)=10.1, 10.3, 23.8, 24.6, 31.2 (2C), 76.2, 80.4, 80.5, 117.0 (9), 117.1 (4), 117.2, 117.3, 137.1 (5), 137.2 (4), 137.5, 137.6, 144.1, 145.2 (2C), 145.7, 146.1, 146.2, 175.9;

HRMS (ESI-TOF) calculated for C$_{39}$H$_{48}$O$_6$N$_4$ (M+Na)$^+$ 691.3472. found 836.3475.

Example 17—Synthesis and Characterization of calix[4]arene tris-O-n-butyl-F$_3$mono-O-acetic acid 76

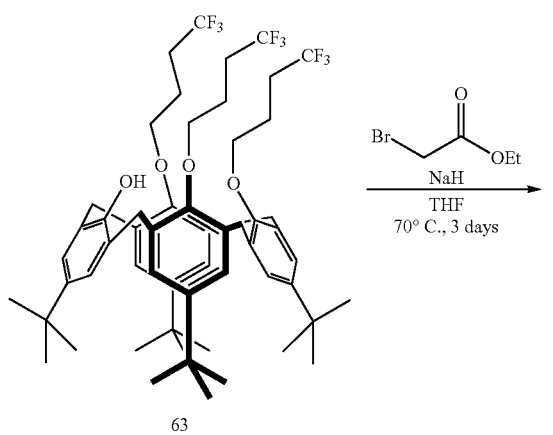

63

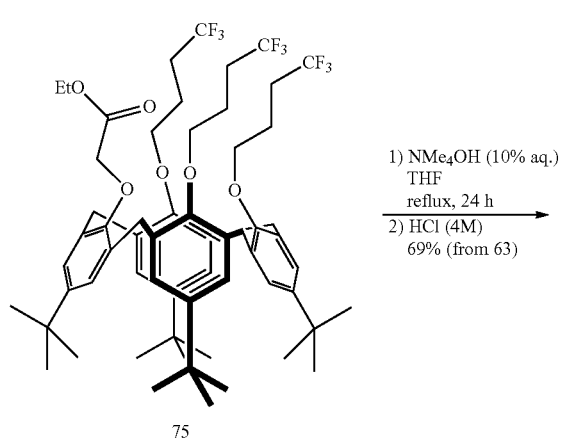

75

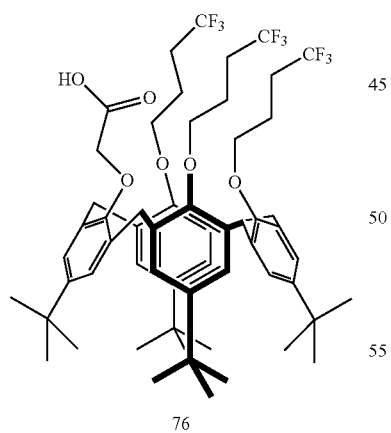

76

Calix[4]arene tris-O-n-butyl-F$_3$ 63 (0.364 g, 0.372 mmol, 1 equiv.) and NaH (60% in oil, 0.070 g, 1.74 mmol, 5 equiv.) were suspended in THF (14 mL), Ethyl bromoacetate (0.420 mL, 3.79 mmol, 10 equiv.) was added and the reaction mixture was stirred for 3 days at 70° C. under inert atmosphere. EtOH (12 mL) was added and the mixture was stirred for 30 minutes at room atmosphere. The mixture was concentrated under reduced pressure and dissolved in CH$_2$Cl$_2$ (50 mL). The organic layer was washed with H$_2$O (3×25 mL) and combined aqueous layers were extracted with CH$_2$Cl$_2$ (2×30 mL). The combined organic layers were concentrated under reduced pressure. The crude residue, calix[4]arene tris-O-n-butyl-F$_3$-mono-(ethyl acetate) 75, was dissolved in THF (20 mL). NMe$_4$OH (10% aq., 30 mL, 0.0331 mol) was added and the reaction mixture was stirred for 24 h at reflux. HCl (4M, 3 mL) was added until pH=1 and the mixture was stifled for 30 minutes at room temperature. THF was concentrated under reduced pressure and the precipitate was filtered and washed with H$_2$O (2×3 mL). The crude residue was purified by flash chromatography (CH$_2$Cl$_2$/MeOH 99:1) to yield compound 76 as a white solid (0.266 g, 0.257 mmol, 69%) which was characterized as follows:

Rf=0.31 (CH$_2$Cl$_2$/MeOH 99:1);

m.p. 136° C.;

IR(cm$^{-1}$): 3292, 2964, 1767, 1482, 1252, 1153, 1148, 1027, 873;

$^1$H NMR (400 MHz, CDCl$_3$, 298K): δ (ppm)=0.84 (s, 18H, tBu), 1.33-1.37 (m, 18H, tBu), 2.07-2.19 (m, 6H, CH$_2$CH$_2$CF$_3$), 2.20-2.34 (m, 6H, CH$_2$CH$_2$CF$_3$), 3.23 (d, $^2$J=12.8 Hz, 2H, ArCH$_2$ eq), 3.27 (d, $^2$J=13.2 Hz, 2H, ArCH$_2$ eq), 3.85 (mult, 4H, OCH$_2$CH$_2$CH$_2$CF$_3$), 4.13-4.19 (m, 4H, ArCH$_2$ ax+OCH$_2$CH$_2$CH$_2$CF$_3$), 4.36 (d, $^2$J=12.4 Hz, 2H, ArCH$_2$ ax), 4.57 (s, 2H, OCH$_2$COOH), 6.52 (s, 2H, ArH), 6.61 (s, 2H, ArH), 7.18 (m, 4H, ArH), 10.89 (sb, 1H, COOH);

$^{13}$C NMR (75 MHz, CDCl$_3$, 298K): δ (ppm)=22.5, 22.8, 30.3, 30.8, 30.9, 31.1 (2C), 31.7, 31.8, 33.8, 34.3, 34.4, 70.7, 74.5, 74.8, 125.1, 125.5, 125.9, 126.3, 127.1 (q, $^1$J=276 Hz), 127.3 (q, $^1$J=274 Hz), 131.6, 132.3, 135.0, 135.1, 145.7, 146.1, 147.8, 150.6, 151.3, 153.7, 169.7;

HRMS (ESI-TOF) calculated for C$_{58}$H$_{73}$O$_6$F$_9$ (M+H)$^+$ 1037.5342. found 1037.5344.

Example 18—Synthesis of calix[4]arene tris-O-n-butyl-F$_3$mono-O-(acetic acid) tetra-NO$_2$ 77

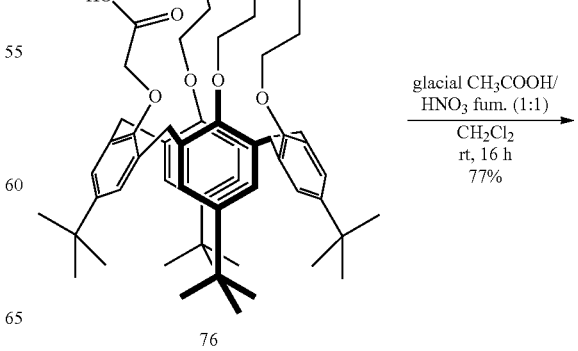

76

-continued

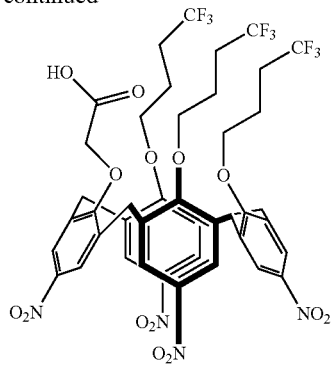

77

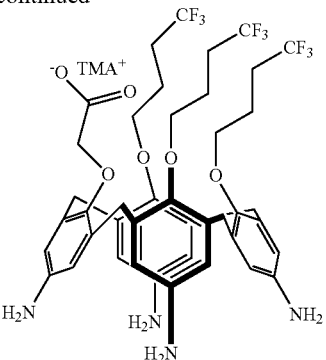

78

Calix[4]arene tris-O-n-butyl-$F_3$ mono-O-acetic acid 76 (0.220 g, 0.212 mmol, 1 equiv.) was dissolved in $CH_2Cl_2$ (20 mL). A mixture of glacial $CH_3COOH$/fuming $HNO_3$ (1:1) (3 mL) was added and the reaction mixture was stirred for 16 hours at room temperature. The reaction mixture was concentrated under reduced pressure and dissolved in $CH_2Cl_2$ (30 mL). The organic layer was washed with $H_2O$ (3×20 mL) and concentrated under reduced pressure. The crude residue was purified by flash chromatography ($CH_2Cl_2$/MeOH 95:5) to yield compound 77 as a yellow solid (0.162 g, 0.163 mmol, 77%) which was characterized as follows:

Rf=0.33 ($CH_2Cl_2$/MeOH 95:5);
m.p. 121-124° C.;
IR(cm$^{-1}$): 3630, 2956, 1755, 1530, 1342, 1254, 1159, 1016, 845;
$^1$H NMR (400 MHz, $CD_3CN$, 298K): δ (ppm)=2.11-2.22 (m, 6H, $CH_2CH_2CF_3$), 2.22-2.30 (mult, 2H, $CH_2CH_2CF_3$), 2.32-2.45 (mult, 2H, $CH_2CH_2CF_3$), 3.57 (m, 4H, $ArCH_2$ eq), 3.96-4.11 (mult, 4H, $OCH_2CH_2CH_2CF_3$), 4.14 (t, $^3J$=7.2 Hz, 2H, $OCH_2CH_2CH_2CF_3$), 4.43 (d, $^2J$=14.0 Hz, 2H, $ArCH_2$ ax), 4.70 (d, $^2J$=14.4 Hz, 2H, $ArCH_2$ ax), 4.78 (s, 2H, $OCH_2COOH$), 7.36 (m, 4H, ArH), 7.89 (m, 4H, ArH); and
$^{13}$C NMR (75 MHz, $CD_3CN$, 298K): δ (ppm)=23.4, 23.6, 30.8, 31.2, 31.4, 31.7, 71.6, 75.4, 75.5, 124.6, 124.7, 125.5, 125.6, 128.5 (q, $^1J$=273 Hz), 128.6 (q, $^1J$=274 Hz), 136.3 (6), 136.4 (1), 137.2, 137.5, 144.1, 144.3, 144.4, 161.9, 162.3, 162.8, 170.5.

Example 19—Synthesis and Characterization of calix[4]arene tris-O-n-butyl-$F_3$mono-O-(acetic acid) tetra-$NH_2$ 78

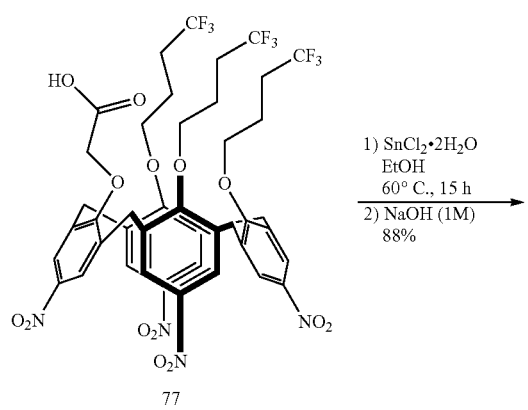

Calix[4]arene tris-O-n-butyl-$F_3$mono-O-acetic acid tetra-$NO_2$ 77 (0.125 g, 0.126 mmol, 1 equiv.) was suspended in EtOH (10 mL). $SnCl_2.2H_2O$ (0.645 g, 2.86 mmol, 23 equiv.) was added and the reaction mixture was stirred for 15 hours at 60° C. NaOH (1M, 10 mL) was added until pH >10 and the precipitate was filtered. $CH_3CN$ (2 mL) was added, the precipitate was filtered and the filtrate was concentrated under reduced pressure. The crude residue was washed with $CH_2Cl_2$ (2×2 mL) to yield compound 78 (0.105 g, 0.111 mmol, 88%) which was characterized as follows:

m.p. 322-324° C. (decomposition);
IR(cm$^{-1}$): 3294, 2922, 1615, 1483, 1257, 1158, 1040, 843;
$^1$H NMR (400 MHz, $CD_3CN$, 298K): δ (ppm)=2.01-2.19 (m, 12H, $CH_2CH_2CF_3$), 2.86 (sb, 27H, TMA), 3.15 (d, $^2J$=12.4 Hz, 2H, $ArCH_2$ eq), 3.21 (d, $^2J$=12.0 Hz, 2H, $ArCH_2$ eq), 3.85-4.03 (m, 14H, $OCH_2CH_2CH_2CF_3$+$NH_2$), 4.07 (d, $^2J$=12.4 Hz, 2H, $ArCH_2$ ax), 4.09 (s, 2H, $OCH_2COOH$), 4.15 (d, $^2J$=12.0 Hz, 2H, $ArCH_2$ax), 6.50 (d, $^4J$=1.8 Hz, 2H, ArH), 6.52-6.54 (m, 4H, ArH), 6.55 (s, 2H, ArH); and
$^{13}$C NMR (75 MHz, $CD_3CN$, 298K): δ (ppm)=22.7, 23.2, 30.1, 30.3, 30.7 (2C), 55.9, 76.5, 76.6, 76.9, 115.8, 115.9, 116.1, 116.3, 127.5*(q, $^1J$=271 Hz), 130.1* (q, $^1J$=273 Hz), 136.8 (8), 136.8 (9), 137.1, 137.2, 143.9, 144.0, 144.3, 146.0, 146.1, 146.4, 172.3;
HRMS (ESI-TOF) calculated for $C_{42}H_{44}O_6F_9N_3$ (M+H)$^+$ 873.3274. found 873.3273.
*These values were determined by HMBC Example 20—Procedure for Calixarene Grafting onto Glassy Carbon 9.8 mg of calix[4]arene tetra-O-n-propyl tetra-$NH_2$ 62 (obtained at example 4) was solubilized in 3 mL aqueous 0.5 M HCl. The solution was introduced in an electrochemical cell put in an ice bath and degassed for 10 minutes. The electrochemical setup consisted of a glassy carbon electrode as working electrode, a platinum grid as counter electrode and a saturated calomel reference electrode as reference. 40 mM aqueous $NaNO_2$ were added and the mixture was stirred for 5 min. The grafting was achieved potentiostatically during 180 s at −0.5 V/SCE. The surfaces were thoroughly rinsed and sonicated in $H_2O$, absolute EtOH, $CH_2Cl_2$ and toluene.

Following the same procedure calix[5]arene penta-O-propyl tetra-$NH_2$ and calix[6]arene hexa-O-propyl tetra-$NH_2$ are also grafted on a glassy carbon electrode.

Example 21—Grafting and Post-Functionalisation of a Gold Substrate with a Ferrocene Redox Moiety Calix[4]arene tris-O-butylCF$_3$ mono-O-(acetic acid) tetra-NH$_2$ 78 (obtained at example 19) is first treated by aqueous HCl, then NaNO$_2$ and potentiostatically grafted onto a gold surface according to a procedure similarly as above-described in example 20. After thorough rinsing in water and absolute EtOH, then drying under argon stream, the modified surfaces were heated under reflux with 40 mmol·L$^{-1}$ of (COCl)$_2$ and 6 mmol·L$^{-1}$ of pyridine in distilled CH$_2$Cl$_2$. After 1 hour, all volatile species were removed under reduced pressure, then a CH$_2$Cl$_2$ solution of 6 mmol·L$^{-1}$ ferrocenylmethylamine was introduced under argon atmosphere with an excess of triethylamine. The system was allowed to react for 2 h 30 min. The post-functionalized surfaces were thoroughly rinsed with CH$_2$Cl$_2$.

Example 22—Characterization of a Grafted Carbon Surface

A carbon substrate coated by compound 62 (as obtained in example 20) was analyzed by atomic force microscopy (AFM) through the scratching technique. The AFM tip was used in contact mode to scratch a rectangular area on the functionalized samples by exercising a sufficient pressure to remove the organic part without damaging the sample. Profiling depth measurements of the scratched area in non contact mode give an average thickness of the layer of 1.2 to 1.4 nm, indicating that the electrografting of the corresponding diazonium cations leads to the formation of an ultrathin layer (here a monolayer).

Example 23—Characterization of a Grafted and Functionalized Gold Surface

The study of the electrochemical response of a gold substrate coated with compound 78 and post-functionalized with ferrocene as described in example 21 allows the quantification of the electroactive immobilized species from the integration of the charge corresponding to the ferrocene-responsive moieties, Since a calixarene frame is able to anchor only one ferrocene redox center, this determination provides a way to estimate the surface concentration of calixarenes onto the substrate. A value c.a. 8 10$^{-11}$ mol·cm$^{-1}$ is found, showing the formation of a monolayer.

Example 24—Mild Conditions Post-Functionalization with Ferrocene Redox Moiety by EDC/NHS Calix[4]arene tetra-O-(acetic acid) tetra-NH$_2$ 70 (as obtained in example 12) was first treated by aqueous HCl, then NaNO$_2$ and then potentiostatically grafted as above-described in example 20. After thorough rinsing in water and absolute EtOH, then drying under argon stream, the modified surfaces were immersed in a MES buffer solution (pH=6.8) containing 3 10$^{-2}$ mol·L$^{-1}$ EDC and 4 10$^{-3}$ mol·L$^{-1}$ NHS and let to react under inert atmosphere for 1 hour, to activate the carboxyl terminal groups of the surface. The surfaces were subsequently rinsed with water and dichloromethane and dried under inert stream. The activated surfaces were then reacted with a CH$_2$Cl$_2$ solution of 6 mmol·L$^{-1}$ ferrocenylmethylamine for 16 hours. The post-functionalized surfaces were thoroughly rinsed with CH$_2$Cl$_2$.

Example 25—Introduction of an Alkyne Moiety and Post-Functionalization with Ferrocene Redox Moiety by Click-Chemistry Calix[4]arene tetra-O-(acetic acid) tetra-NH2 70 was first treated by aqueous HCl, then NaNO$_2$ and potentiostatically grafted as above-described. After thorough rinsing in water, absolute EtOH, CH$_2$Cl$_2$ and toluene, then drying under argon stream, the modified surfaces were reacted for 16 h under inert atmosphere at room temperature with 6 mmol·L$^{-1}$ of propargylamine and 30 mmol·L$^{-1}$ of triethylamine in distilled CH$_2$Cl$_2$. After 16 h, all volatiles were removed under reduced pressure, then a THF solution of 0.8 mol·L$^{-1}$ ferrocenylmethylazido and an aqueous solution of 6.4 mol·L$^{-1}$ copper sulfate were introduced under argon atmosphere. An aqueous solution of 9.2 mol·L$^{-1}$ ascorbic acid and of 38 mol·L$^{-1}$ NaHCO$_3$ were also introduced. The system was allowed to react for 1 h. The post-functionalized surfaces were thoroughly rinsed with H$_2$O, acetone, THF and CH$_2$Cl$_2$.

Example 26—Synthesis and Characterization of calix[4]arene tetra-O-propyl tetra-diazonium 79

Calix[4]arene tetra-O-propyl tetra-aniline 62 (0.102 g, 0.156 mmol, 1 equiv.) was solubilized in 1 mL of acetonitrile. At −40° C., NOBF$_4$ (0.096 g, 0.822 mmol, 5 equiv.) was added and the reaction mixture was stirred for 1 h 30 at −40° C. under inert atmosphere. The reaction mixture was concentrated under reduced pressure at room temperature. The crude residue was then washed with diethylether (1×0.5 mL) and with EtOH (3×0.5 mL) to yield calix[4]arene tetra-O-propyl tetra-diazonium 79 (0.125 g, 0.119 mmol, 77%) which was characterized as follows:

IR(cm$^{-1}$): 3172, 3005, 2943, 2254, 1479, 1035, 833;
$^1$H NMR (300 MHz, CD$_3$CN, 298K): δ (ppm)=1.01 (t, $^3$J=7.5 Hz, 12H, CH$_2$CH$_3$), 1.93 (mult, 8H, CH$_2$CH$_3$), 3.77 (d, $^2$J=14.7 Hz, 4H, ArCH$_2$ eq), 4.21 (t, $^3$J=7.5 Hz, 8H, OCH$_2$), 4.56 (d, $^2$J=14.4 Hz, 4H, ArCH$_2$ ax), 8.05 (s, 8H, ArH).

Example 27—Synthesis and Characterization of calix[4]arene tetra-O-butylCF$_3$ tetra-diazonium 80

Calix[4]arene tetra-O-butylCF$_3$ tetra-aniline 66 (0.101 g, 0.109 mmol, 1 equiv.) as obtained in example 8 was solubilized in 1 mL of acetonitrile. At −40° C., NOBF$_4$ (0.067 g, 0.574 mmol, 5 equiv.) was added and the reaction mixture was stirred for 1 h 30 at −40° C. under inert atmosphere. The reaction mixture was concentrated under reduced pressure at room temperature. The crude residue was then washed with diethylether (1×0.5 mL) and with EtOH (3×0.5 mL) to yield calix[4]arene tetra-O-butylCF$_3$ tetra-diazonium 80 (0.145 g, 0.109 mmol, 100%) which was characterized as follows:

IR(cm$^{-1}$): 3005, 2940, 2272, 1376, 1073, 766;
$^1$H NMR (300 MHz, CD$_3$CN, 298K): δ (ppm)=2.06-2.31 (m, 16H, CH$_2$CH$_2$CF$_3$), 3.82 (d, $^2$J=14.7 Hz, 4H, ArCH$_2$ eq), 4.24 (t, $^3$J=7.2 Hz, 8H, OCH$_2$), 4.47 (d, $^2$J=14.4 Hz, 4H, ArCH$_2$ ax), 8.07 (s, 8H, ArH).

Example 28—Synthesis and Characterization of calix[4]arene tris-O-propyl mono-O-acetic acid tetra-diazonium 81

Calix[4]arene tris-O-propyl mono-O-(acetic acid) tetra-aniline 74 (0.090 g, 0.130 mmol, 1 equiv.) as obtained in example 16 was solubilized in 1 mL of acetonitrile. At −40° C., NOBF$_4$ (0.088 g, 0.753 mmol, 5 equiv.) was added and the reaction mixture was stirred for 1 h 30 at −40° C. under inert atmosphere. The reaction mixture was concentrated under reduced pressure at room temperature. The crude residue was then washed with diethylether (1×0.5 mL) and with EtOH (3×0.5 mL) to yield calix[4]arene tris-O-propyl mono-O-(acetic acid) tetra-diazonium 81 (0.096 g, 0.098 mmol, 76%) which was characterized as follows:

IR(cm$^{-1}$): 3369, 3060, 2991, 2272, 2261, 1425, 1267, 1102, 1037, 832;

$^1$H NMR (300 MHz, CD$_3$CN, 298K): δ (ppm)=0.97-1.04 (m, 9H, CH$_2$CH$_3$), 1.94 (mult, 6H, CH$_2$CH$_3$), 3.55 (d, $^2$J=14.1 Hz, 2H, ArCH$_2$ eq), 3.53 (d, $^2$J=14.1 Hz, 2H, ArCH$_2$ eq), 3.74-3.84 (m, 6H, OCH$_2$CH$_2$CH$_3$), 4.56 (d, $^3$J=14.7 Hz, 2H, ArCH$_2$ ax), 4.78 (d, $^2$J=14.7 Hz, 2H, ArCH$_2$ ax), 7.99 (sb, 4H, ArH), 8.13 (sb, 4H, ArH).

Example 29—Synthesis and Characterization of calix[4]arene tetra-O-(acetic acid) tetra-diazonium 82

Calix[4]arene tetra-O-(acetic acid) tetra-aniline 70 (0.101 g, 0.106 mmol, 1 equiv.) as obtained in example 12 was solubilized in 1 mL of acetonitrile. At −40° C., NOBF$_4$ (0.064 g, 0.548 mmol, 5 equiv.) was added and the reaction mixture was stirred for 1 h 30 at −40° C. under inert atmosphere. The reaction mixture was concentrated under reduced pressure at room temperature. EtOH (0.5 mL) was added to the crude residue and the filtrate was concentrated under reduced pressure. The residue was then washed with ether (2×0.5 mL) to yield calix[4]arene tetra-O-(acetic acid) tetra-diazonium 82 (0.065 g, 0.0855 mmol, 81%) which was characterized as follows:

$^1$H NMR (300 MHz, (CD$_3$)$_2$O. 298K): δ (ppm)=3.98 (d, $^2$J=15.3 Hz, 4H, ArCH$_2$ eq), 5.11 (s, 8H, OCH$_2$), 5.18 (d, $^2$J=14.1 Hz, 4H, ArCH$_2$ ax), 8.40 (s, 8H, ArH).

Example 30—Synthesis and Characterization of calix[4]arene tetra-O-butyl-F$_3$ tetra-diazonium 80 with Another Methodology Calix[4]arene tetra-O-butyl-F$_3$ tetra-aniline 66 (0.051 g, 0.0540 mmol, 1 equiv.) as obtained in example 8 was solubilized in 1 mL of HBF$_4$. At −4° C., an aqueous solution of NaNO$_2$ (0.072 g, 1.04 mmol, 19 equiv.) was slowly added and the reaction mixture was stirred for 10 minutes at −4° C. under inert atmosphere. The crude residue was then filtered and washed with H$_2$O (3×0.5 mL) to yield calix[4]arene tetra-O-butyl-F$_3$ tetra-diazonium 80 (0.063 g, 0.480 mmol, 89%) which was characterized as follows:

IR(cm$^{-1}$): 3005, 2940, 2272, 1376, 1073, 766;

$^1$H NMR (300 MHz, CD$_3$CN, 298K): δ (ppm)=2.06-2.31 (m, 16H, CH$_2$CH$_2$CF$_3$), 3.82 (d, $^2$J=14.7 Hz, 4H, ArCH$_2$ eq), 4.24 (t, $^3$J=7.2 Hz, 8H, OCH$_2$), 4.47 (d, $^2$J=14.4 Hz, 4H, ArCH$_2$ ax), 8.07 (s, 8H, ArH).

Example 31—Synthesis of Gold Nanoparticles Stabilized with calix[4]arene tetra-O-butylCF$_3$ Gold chloride hydrate (0.05 g, 0.127 mmol, 1 equiv.) was solubilized in 50 mL of acetonitrile. Under inert atmosphere and at 0° C., calix[4]arene tetra-O-butylCF$_3$ tetra-diazonium 80 (0.097 g, 0.735 mmol, 0.53 equiv.) obtained in example 27 solubilized in 50 mL of acetonitrile was added. The reaction mixture was vigorously stirred and an aqueous solution of 0.296 mol·L$^{-1}$ NaBH$_4$ was added drop by drop. After 2 hours, the nanoparticles were separated from solution via centrifugation at 8000 rpm for 10 minutes. The AuNP pellet was washed with CH$_2$Cl$_2$ and was redispersed in acetone.

Example 32—Modification of Multi-Walled Carbon Nanotubes (MWNT) with calix[4]arene tetra-O-butylCF$_3$ a) Buckypaper Preparation Buckypaper is known in the art as a thin and uniform sheet made from an aggregate of carbon nanotubes. MWNT (1 mg) was dispersed in EtOH (200 mL) in an ultrasonic bath for 30 minutes. The dispersion was filtrated over a Teflon or nylon membrane and the buckypaper was then dried at 68° C. for 30 minutes.

b) Buckypaper Modification 8.2 mg of calix[4]arene tetra-O-butylCF$_3$ tetra-diazonium 80 (obtained in example 27) was solubilized in 6 mL aqueous solution of 0.1 mol·L$^{-1}$ Bu$_4$N$^+$PF$_6^-$. The solution was introduced in an electrochemical cell put in an ice bath and degassed for 10 minutes. The electrochemical setup consisted of the buckypaper as working electrode, a platinum grid as counter electrode and a saturated calomel reference electrode as reference. The grafting was achieved potentiostatically during 30 minutes at −1 V/SCE. The surfaces were thoroughly rinsed and sonicated in H$_2$O, absolute EtOH, CH$_2$Cl$_2$ and toluene.

c) X-Ray Photoelectron Spectroscopy (XPS) Analysis

XPS analysis of the modified buckypaper surface shows the F$_{1s}$ peak at 689.6 eV and the C$_1$ at 292.8 eV that are characteristic of CF$_3$ groups.

Example 33—Modification of Single-Walled Carbon Nanotubes (SWNT) with calix[4]arene tetra-O-n-butyl-F3 a) Buckypaper Preparation and Modification

The preparation of the buckypaper of SWNT and the grafting of the calix[4]arene tetra-O-butylCF3 tetra-diazonium 80 (obtained in example 27) are realized according to a procedure similarly as above-described in example 32.

b) Raman Analysis

Raman analysis of the modified buckypaper surface shows spectral features that are characteristic of a covalent functionalization of SWNT.

The invention claimed is:

1. A material grafted on its surface with an ultra-thin layer of one or more substituted (thia)calix[n]aryls, as represented below

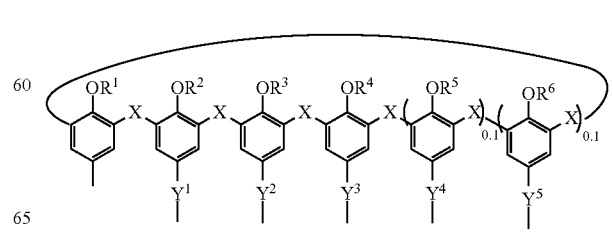

wherein
- n is the number of aryl moieties forming the (thia)calix[n]aryl ring being 4, 5, or 6; X represents $CH_2$, S, SO or $SO_2$;
- a carbon of one arene ring of the (thia)calix[n]aryls being covalently and directly anchored to the material's surface;
- $R^1$, $R^2$, $R^3$, $R^4$, $R^5$ and $R^6$ each independently represent hydrogen or $C_{1-30}$ alkyl optionally substituted with one or more substituents each independently selected from the group consisting of halo, carboxylic acid ester, alkyl or benzyl thioester, alkenyl, alkynyl, $C_{1-30}$ alkoxy, aryl, substituted aryl (wherein the substituent is fluoro or cyano or $C_{1-30}$ alkyl or $C_{1-30}$ alkoxy), $—N_3$, cyano, carboxylic acid, carboxylic acid amide, —OH, amino, amido, imino, carbamate, acyl chloride, ureido, thioureido, mercapto, substituted disulfide, heterocyclic, amino acid and amino acid derivative, peptide, phosphine or phosphine oxide, crown ether, aza-crown ether, cryptand, porphyrin, calixarene, cyclodextin, resorcinarene, saccharide, and polyethylene glycol; and wherein two or more of $R^1$, $R^2$, $R^3$, $R^4$, $R^5$ and $R^6$ may be covalently linked either directly or by a bridge that includes oxygen, phosphine, phosphine oxide, sulfur, SO, $SO_2$, amino, imino, amido, ureido, thioureido, ester, thioester, alkene, alkyne or alkyl;
- $Y^1$—, $Y^2$—, $Y^3$—, $Y^4$— and $Y^5$— each independently represent a covalent link with the material's surface, or $Y^1$—, $Y^2$—, $Y^3$—, $Y^4$— and $Y^5$— are each independently selected from the group consisting of OH, hydrogen, $NO_2$, halogen, $N_2^+A^-$, wherein $A^-$ is an anion, $C_{1-30}$ alkyl, carboxylic acid and derivatives thereof, acyl, $—N_3$, alkenyl, and alkynyl.

2. The material according to claim 1, wherein the ultra-thin layer grafted on the surface of the material is a monolayer.

3. The material according to claim 1, wherein the material is a conductor, semiconductor, insulator, a composite material, a nanoparticle, a polymer, or a nanotube.

4. The material according to claim 1, wherein X is methylene and the indexes 0,1 at the right sides of the aryl moieties bearing $R^5$ and $R^6$ are both 0.

5. The material according to claim 1, wherein $R^2$, $R^3$, and $R^4$ and, if present, $R^5$ and $R^6$ have the same meaning while $R^1$ has a different meaning; or wherein all of $R^1$, $R^2$, $R^3$, $R^4$, $R^5$, and $R^6$, have the same meaning.

6. The material according to claim 1, wherein $R^1$, $R^2$, $R^3$, $R^4$, $R^5$, and $R^6$, are each independently a hydrogen or an optionally substituted $C_1$-$C_{30}$ alkyl.

7. The material according to claim 1, wherein of $R^1$, $R^2$, $R^3$, $R^4$, $R^5$, and $R^6$ are n-propyl, $—CH_2—COOH$, $—CH_2—COOC_1$-$C_4$ alkyl, or $—(CH_2)_3—CF_3$.

8. The material according to claim 1, wherein all of $Y^1$, $Y^2$, $Y^3$, and if present, $Y^4$ and $Y^5$ are the same.

9. The material according to claim 1, wherein the immobilized (thia)calix[n]arenes are post-functionalized through the anchoring of chemical species selected from molecules, nanoparticles, biomolecules, ligands for metal ions or anions, molecular receptors, oligomers and polymers.

10. The material according to claim 1, wherein the ultra-thin layer has a thickness from 1 nm to 4 nm.

11. The material according to claim 10, wherein n is 4.

12. The material according to claim 10, being selected from the group consisting of metals, metal alloys, metal compounds, metal oxides, nanoparticles, carbon, glass beads, silica, and silicon wafers.

13. The material according to claim 12, wherein said metal or metal oxide is selected from the group consisting of gold, silver, nickel, iron oxide, and titanium oxide.

14. The material according to claim 12, wherein said carbon is in the form of nanotubes.

15. The material according to claim 12, wherein said nanoparticles are selected from the group consisting of gold, silver, selenium, iron oxide, and titanium oxide.

16. A process of grafting the material of claim 1 with (thia)calix[n]aryl groups via their large rim, comprising grafting on the surface of the material as an ultra-thin layer of (thia)calix[n]aryl groups by electrochemical reduction, homogeneous reduction with a reactant, or thermal reduction of substituted (thia)calix[n]aryl salts of formula I:

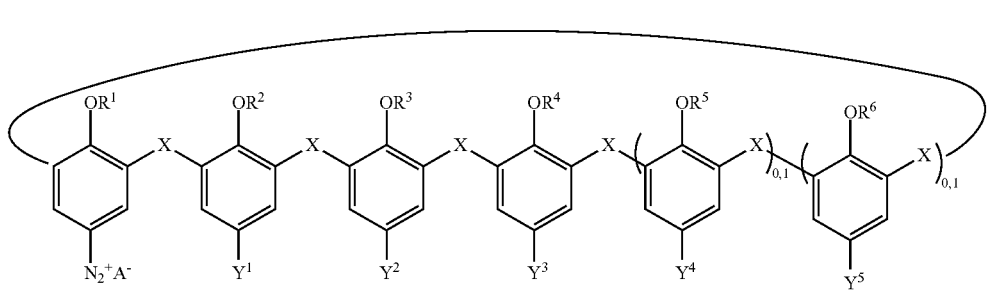

(I)

, wherein $A^-$ is an anion;

$R^1$, $R^2$, $R^3$, $R^4$, $R^5$ and $R^6$ are as defined in claim 1;

$Y^1$, $Y^2$, $Y^3$, $Y^4$ and $Y^5$ are each independently selected from the group consisting of OH, H, $NO_2$, halogen, $C_{1-30}$ alkyl, acyl, carboxylic acid and derivatives thereof, $-N_3$, alkenyl, alkynyl and $N_2^+A^-$; and wherein a carbon of one arene ring of the (thia)calix[n]aryls is covalently and directly anchored to the material's surface.

* * * * *